(12) United States Patent
Umezawa et al.

(10) Patent No.: US 10,997,762 B2
(45) Date of Patent: May 4, 2021

(54) IMAGE DISPLAY SYSTEM, IMAGE DISPLAY METHOD, AND PROGRAM

(71) Applicant: CANON KABUSHIKI KAISHA, Tokyo (JP)

(72) Inventors: Kohtaro Umezawa, Tokyo (JP); Mitsuhiro Shingu, Yokohama (JP); Kazuhito Oka, Tokyo (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 16/331,837

(22) PCT Filed: Oct. 3, 2017

(86) PCT No.: PCT/JP2017/035994
§ 371 (c)(1),
(2) Date: Mar. 8, 2019

(87) PCT Pub. No.: WO2018/066563
PCT Pub. Date: Apr. 12, 2018

(65) Prior Publication Data
US 2019/0378314 A1     Dec. 12, 2019

(30) Foreign Application Priority Data

Oct. 7, 2016   (JP) .............................. JP2016-198891

(51) Int. Cl.
*G06T 11/60*     (2006.01)
*G16H 30/20*     (2018.01)
(Continued)

(52) U.S. Cl.
CPC ............ *G06T 11/60* (2013.01); *G06T 11/001* (2013.01); *G16H 30/20* (2018.01); *G16H 30/40* (2018.01);
(Continued)

(58) Field of Classification Search
None
See application file for complete search history.

(56) References Cited

U.S. PATENT DOCUMENTS

2007/0109402 A1   5/2007  Niwa
2011/0021924 A1*  1/2011  Sethuraman ........... A61B 8/445
                                                      600/463
(Continued)

FOREIGN PATENT DOCUMENTS

EP    2034715 A1    3/2009
EP    2674108 A1   12/2013
(Continued)

*Primary Examiner* — Nurun N Flora
(74) *Attorney, Agent, or Firm* — Canon U.S.A., Inc. IP Division

(57) ABSTRACT

The present invention provides an image display system which can simplify an operation of an operator for displaying images appropriate for diagnosis. An image display system according to the present invention includes a first obtaining unit configured to obtain first image data piece, a second obtaining unit configured to obtain a first meta-information piece regarding the first image data piece, a third obtaining unit configured to obtain a second image data piece, a fourth obtaining unit configured to obtain a second meta-information piece regarding the second image data piece, and a display control unit configured to determine a superimposition style corresponding to a combination of the first and second meta-information pieces based on the first and second meta-information pieces and display a superimposition image of the first and second image data pieces in the superimposition style on a display unit.

18 Claims, 22 Drawing Sheets

(51) Int. Cl.
- *G16H 30/40* (2018.01)
- *G06T 11/00* (2006.01)
- *A61B 5/00* (2006.01)
- *A61B 8/00* (2006.01)

(52) U.S. Cl.
CPC ............ *A61B 5/0095* (2013.01); *A61B 8/463* (2013.01); *G06T 2210/41* (2013.01)

(56) References Cited

U.S. PATENT DOCUMENTS

| | | | |
|---|---|---|---|
| 2012/0223969 A1 | 9/2012 | Schoeller | |
| 2013/0120453 A1* | 5/2013 | Carmi | G06T 5/50 345/634 |
| 2013/0129198 A1* | 5/2013 | Sherman | G06F 19/321 382/159 |
| 2015/0363979 A1 | 12/2015 | Takano | |

FOREIGN PATENT DOCUMENTS

| | | |
|---|---|---|
| JP | 2005-218684 A | 8/2005 |
| JP | 2007-190212 A | 8/2007 |
| JP | 2011-137695 A | 7/2011 |
| JP | 2015-150029 A | 8/2015 |
| WO | 2010/113479 A1 | 10/2010 |
| WO | 2010/143103 A1 | 12/2010 |
| WO | 2013/111684 A1 | 8/2013 |
| WO | 2014/181633 A1 | 11/2014 |

\* cited by examiner

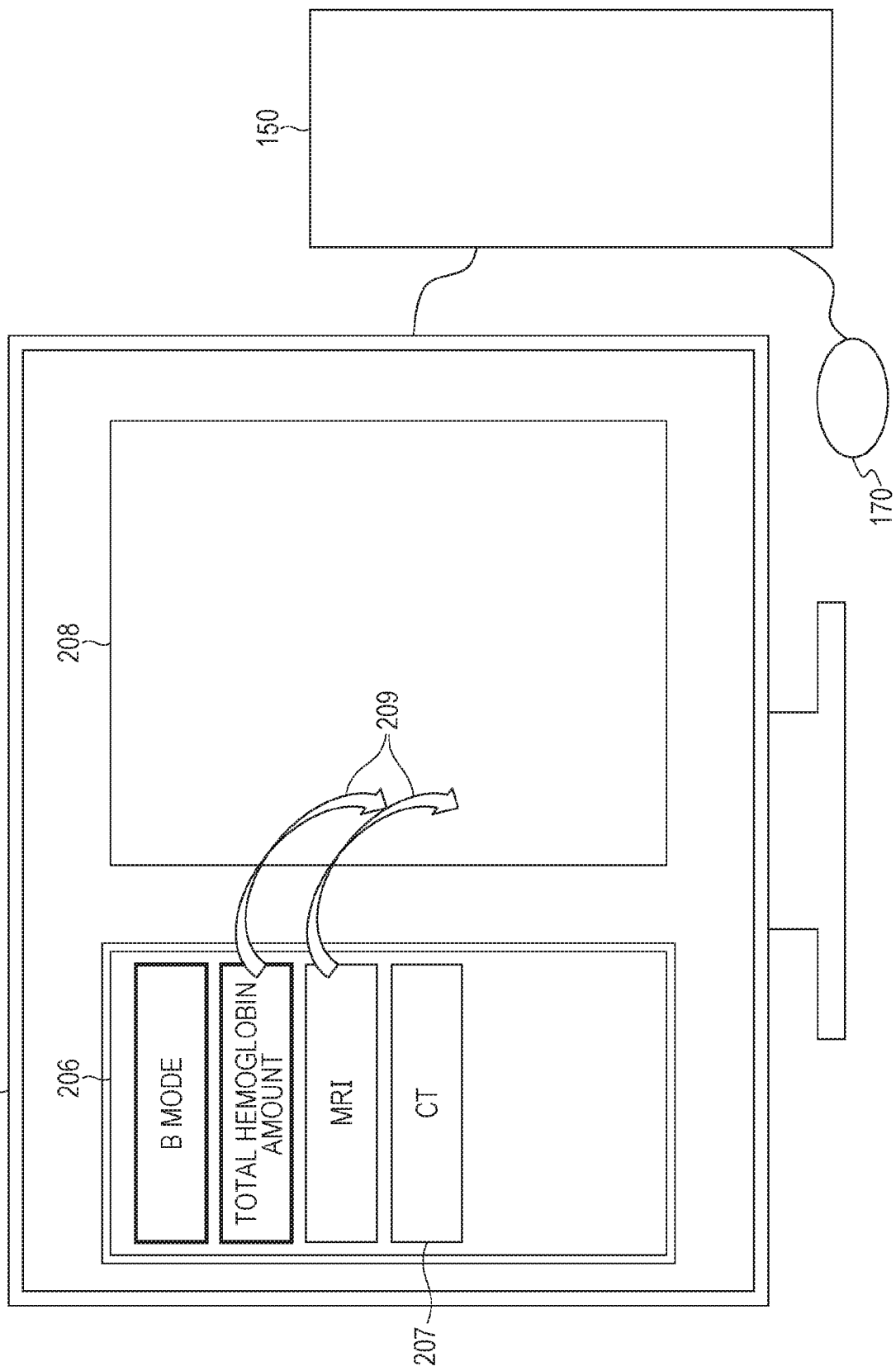

FIG. 6

| No. | IMAGE TYPE | DISPLAY IMAGE | | | |
|---|---|---|---|---|---|
| 1 | B MODE<br>TOTAL HEMOGLOBIN AMOUNT | DISPLAY IMAGE 1 | DISPLAY IMAGE 2 | Null | ... |
| 2 | B MODE<br>TOTAL HEMOGLOBIN AMOUNT<br>OXYGEN SATURATION | DISPLAY IMAGE 3 | DISPLAY IMAGE 4 | DISPLAY IMAGE 5 | ... |
| 3 | ⋮ | ⋮ | ⋮ | ⋮ | |

FIG. 7

| No. | DISPLAY IMAGE | SUPERIMPOSED ORDER (FROM LOWEST LAYER) | COLORING (FROM LOWEST LAYER) | DISPLAY REGION (VERTICAL, HORIZONTAL) |
|---|---|---|---|---|
| 1 | DISPLAY IMAGE 1 | B MODE | GRAY SCALE | (1, 1) |
| | DISPLAY IMAGE 2 | B MODE<br>TOTAL HEMOGLOBIN AMOUNT | GRAY SCALE<br>RED | (1, 2) |
| 2 | DISPLAY IMAGE 3 | B MODE | GRAY SCALE | (1, 1) |
| | DISPLAY IMAGE 4 | B MODE<br>TOTAL HEMOGLOBIN AMOUNT | GRAY SCALE<br>YELLOW | (1, 2) |
| | DISPLAY IMAGE 5 | B MODE<br>OXYGEN SATURATION | GRAY SCALE<br>RED TO BLUE | (1, 3) |
| 3 | ⋮ | ⋮ | ⋮ | ⋮ |

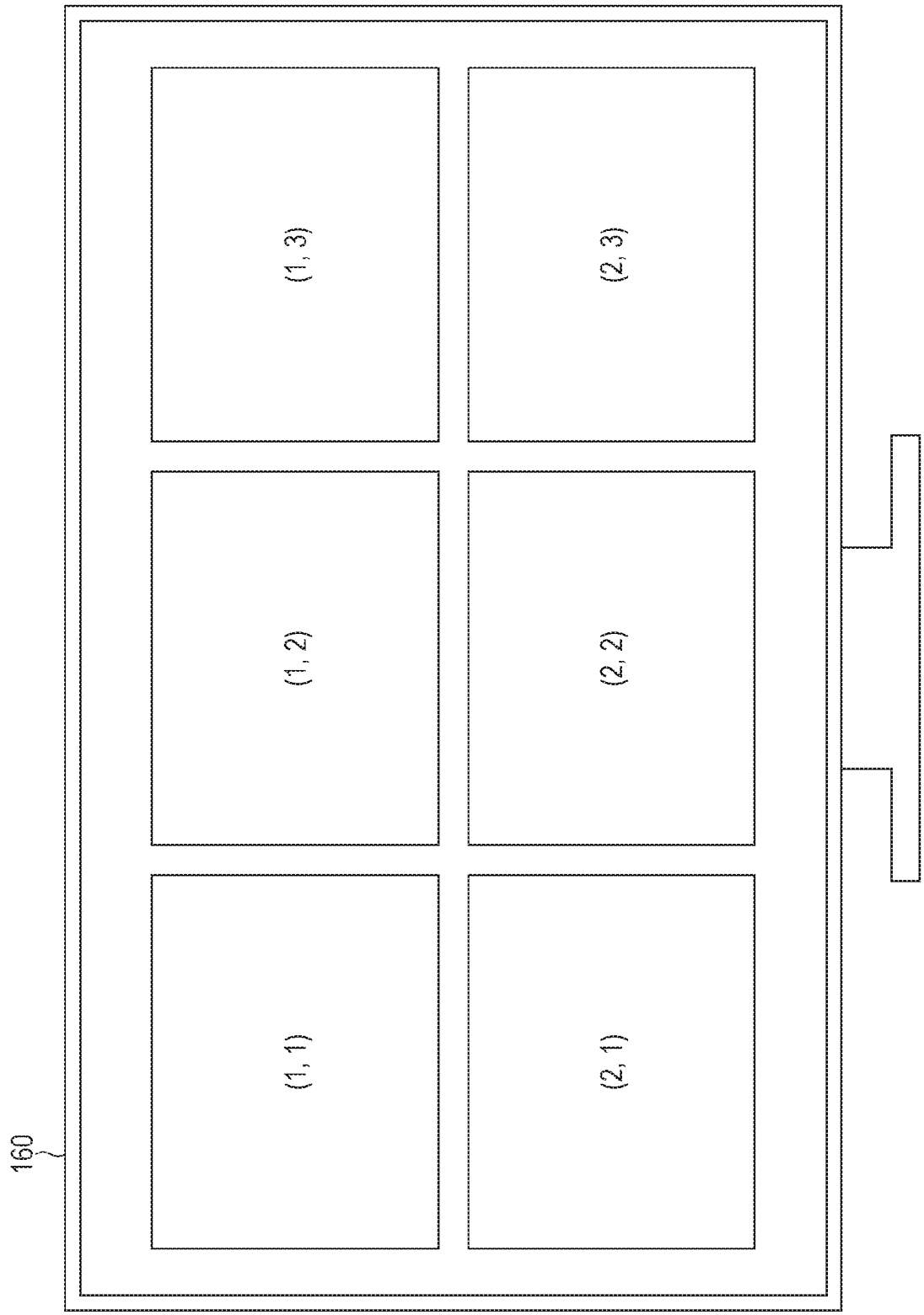

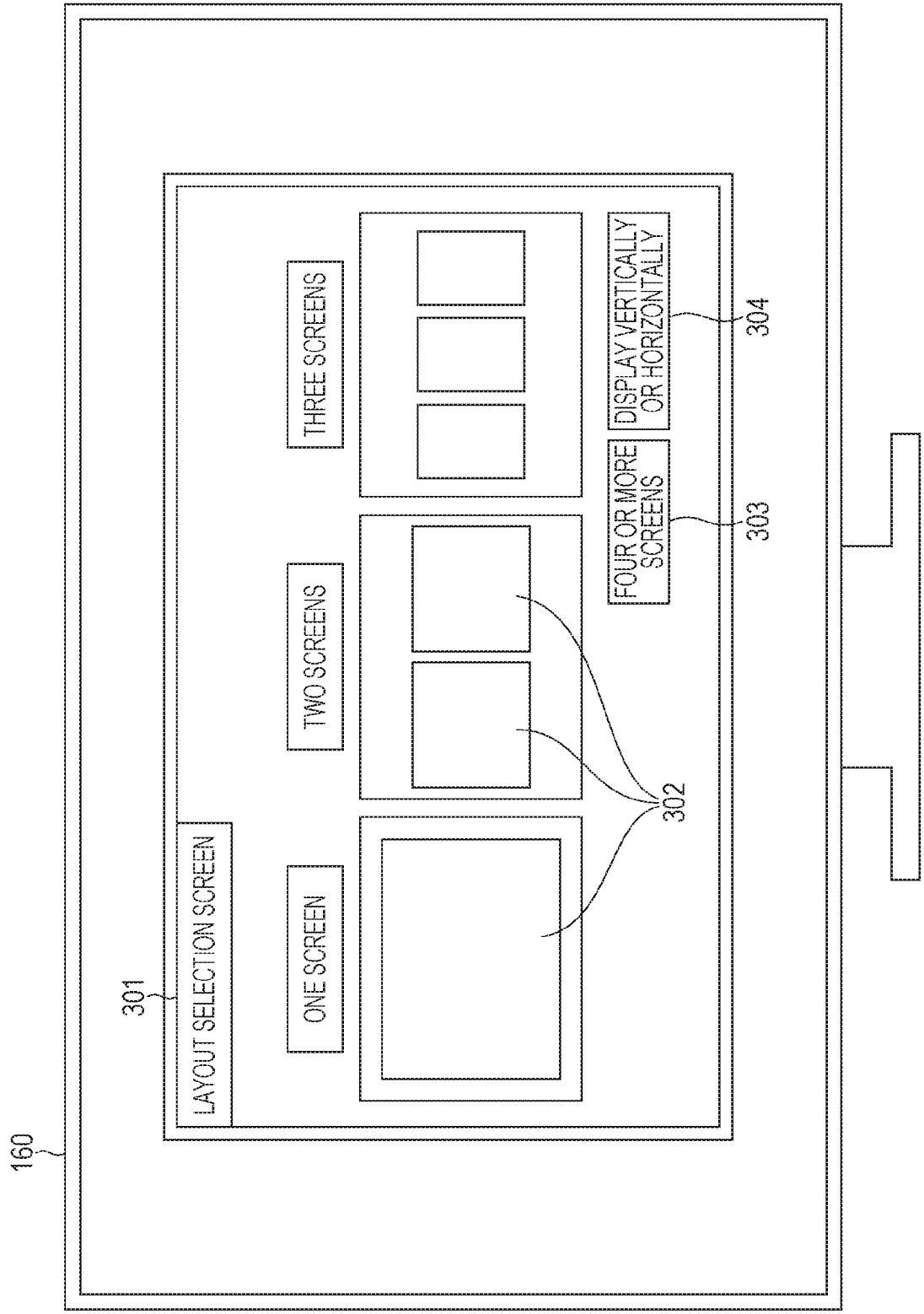

FIG. 12

"OXYGEN SATURATION" AND "TOTAL
HEMOGLOBIN AMOUNT" ARE NOT SET TO BE
SUPERIMPOSED. WILL YOU EXECUTE
SUPERIMPOSITION?

"TOTAL HEMOGLOBIN AMOUNT" WILL BE
DISPLAYED IN "GRAY SCALE".

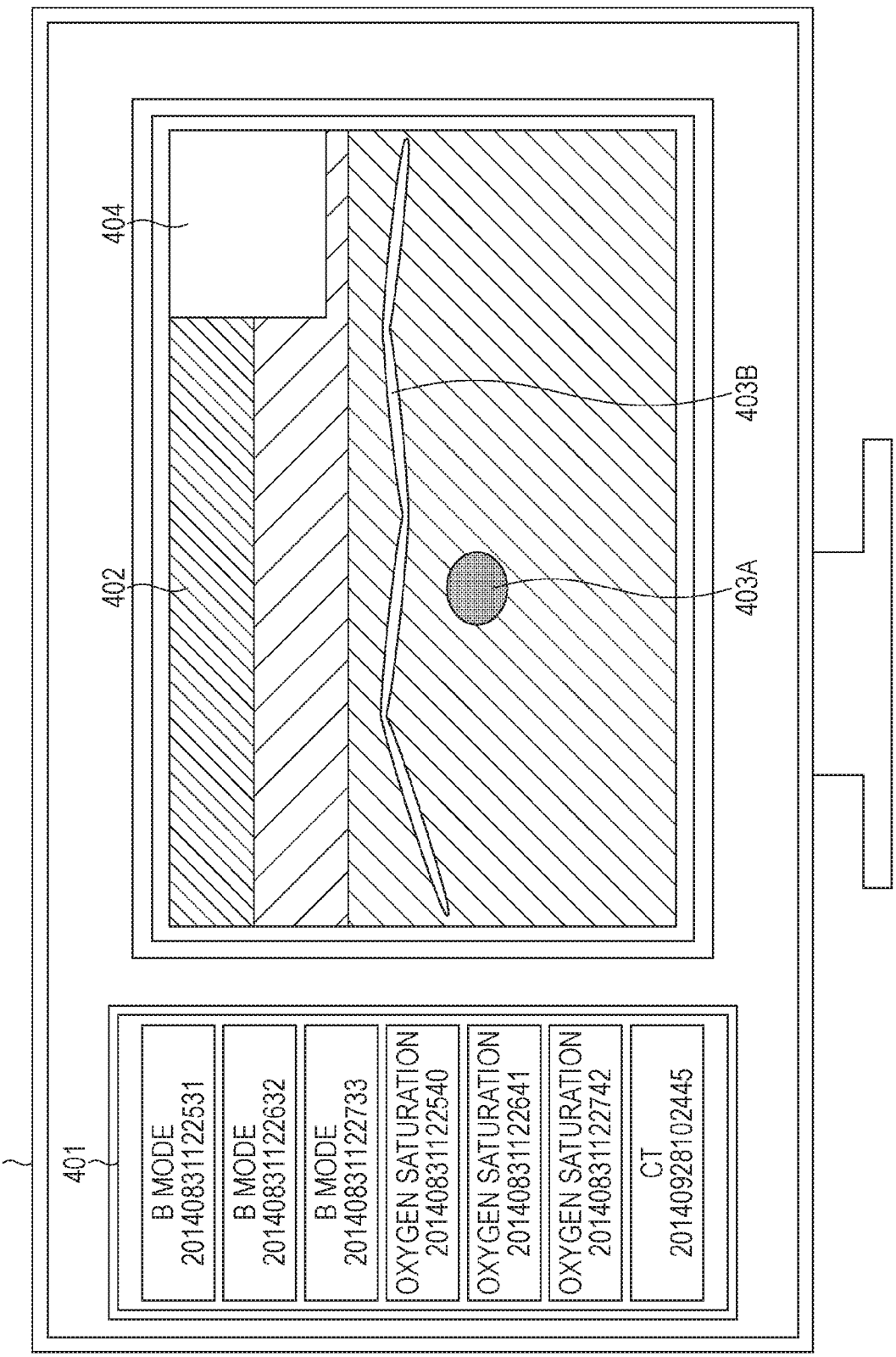

FIG. 14

| filename: OXYGEN SATURATION IMAGE | filename: B MODE IMAGE |
|---|---|
| data: OXYGEN SATURATION | data: B MODE |
| date: 2014/08/31 12:25:40 | date: 2014/08/31 12:25:31 |
| color map: blue~green~red | color map: grayscale |
| patient ID: 12235654 | patient ID: 12235654 |
| device: PA mammography | device: Ultrasonic |
| hospital: XXX hospital | hospital: XXX hospital |
| frame number: 1, single | frame number: 1, single |
| superimposition target: US Bmode, 12235654, 20140831122531 | superimposition target: PA mammo, 12235654, 20140831122748 |
| superimposed order: 1 | superimposed order: 2 |
| position: (x, y, z) = (12, 15, 16) | position: (x, y, z) = (12, 15, 16) |

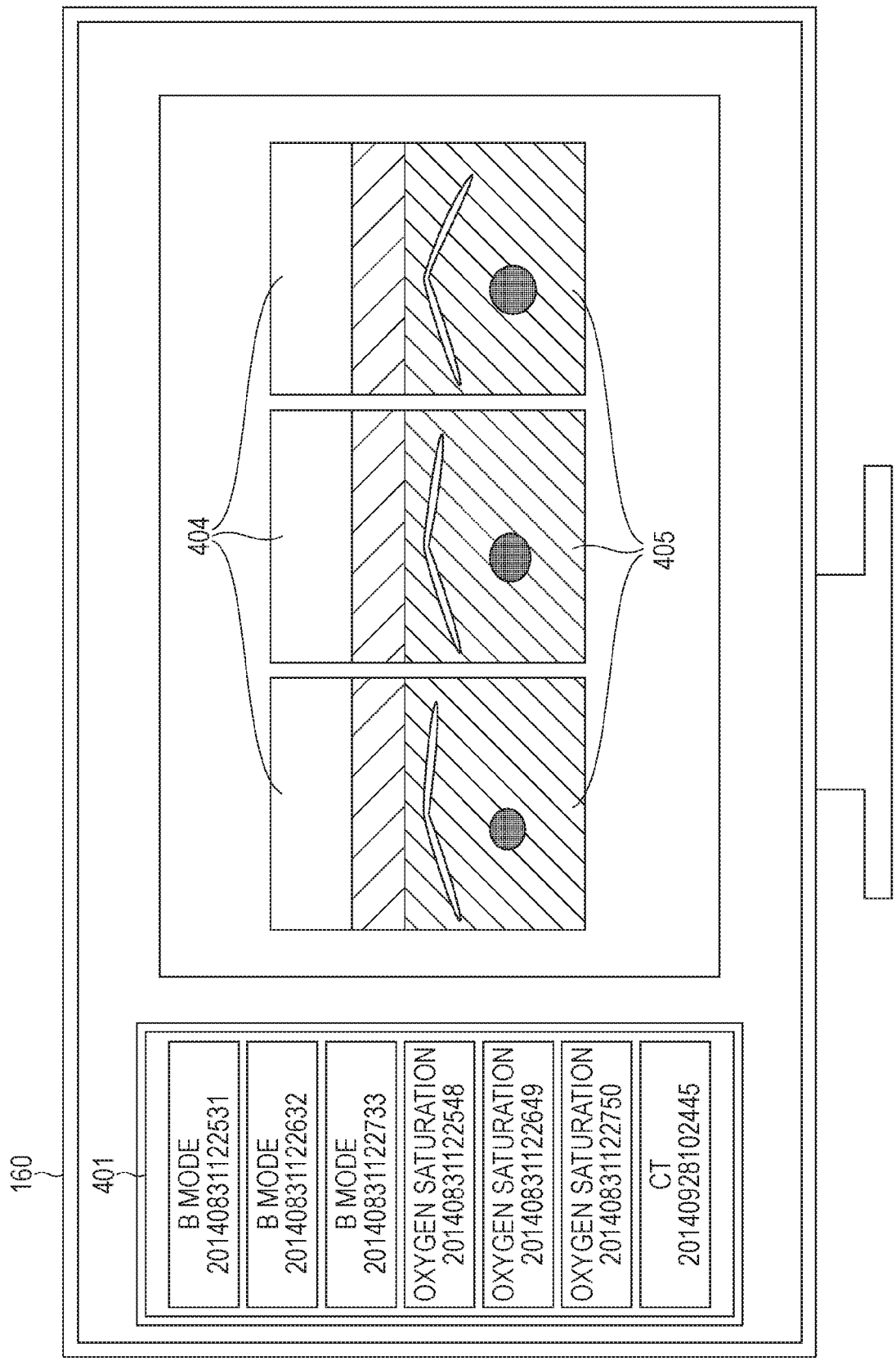

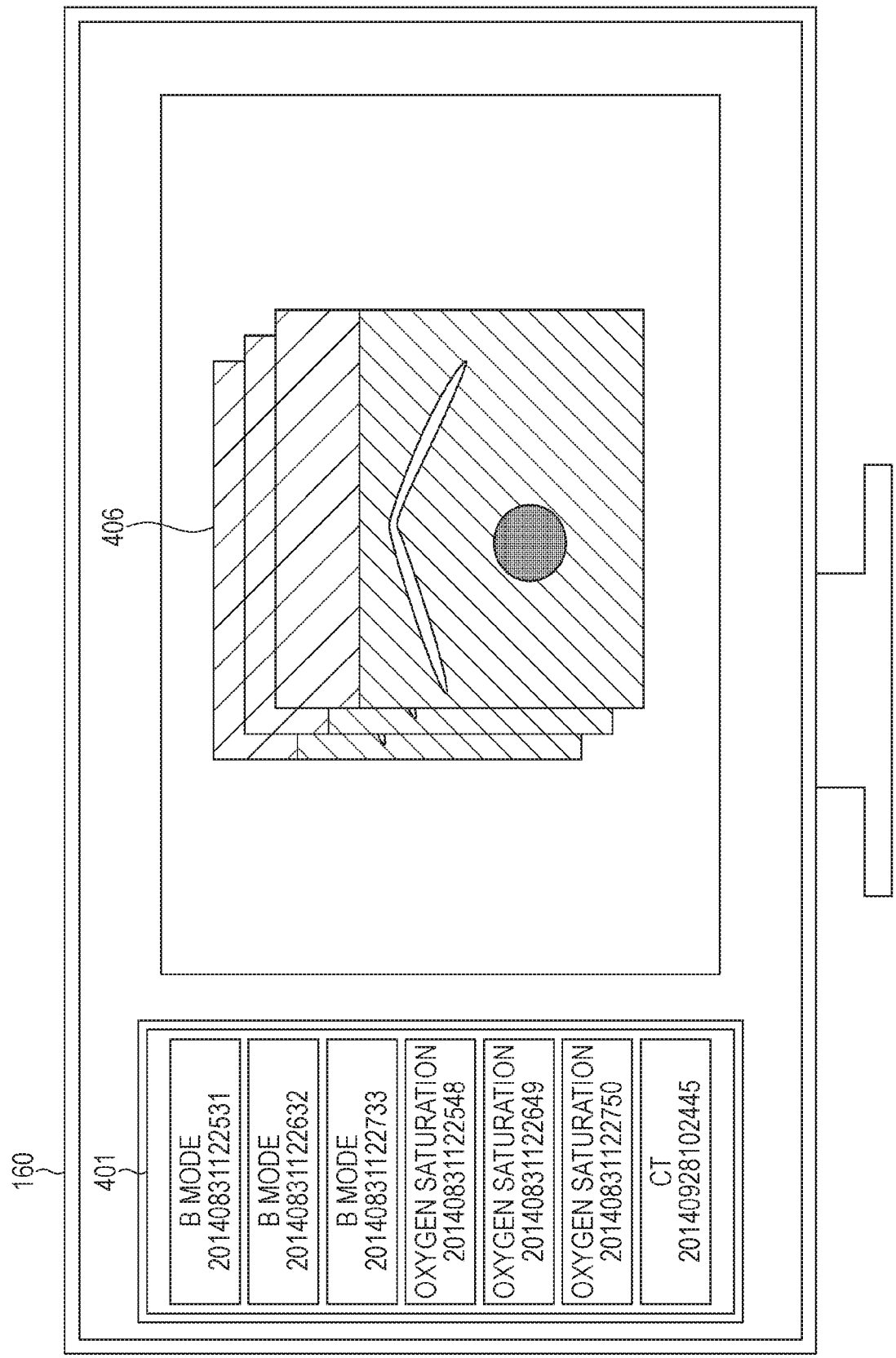

IMAGE DISPLAY SYSTEM, IMAGE DISPLAY METHOD, AND PROGRAM

TECHNICAL FIELD

The present invention relates to an image display system and an image display method.

BACKGROUND ART

For improved diagnosability in medical diagnoses, a plurality of images different from each other is superimposed for display by using a display application so that the resulting superimposition image can be used for diagnosing. PTL 1 discloses superimposition of a photoacoustic image and an ultrasound image.

CITATION LIST

Patent Literature

PTL 1: Japanese Patent Laid-Open No. 2005-218684

SUMMARY OF INVENTION

For example, in order to display a superimposition image of a plurality of images different from each other on a general viewer, an operator may be required to adjust detail display parameters on a display application. In this case, the operator may need to set display parameters appropriate for the image type of images to be superimposed for every diagnosis, complicating an operation of the operator.

Accordingly, the present invention provides an image display system which can simplify an operation of an operator for displaying an image appropriate for a diagnosis.

An image display system according to the present invention includes a first obtaining unit configured to obtain first image data piece, a second obtaining unit configured to obtain a first meta-information piece regarding the first image data piece, a third obtaining unit configured to obtain a second image data piece, a fourth obtaining unit configured to obtain a second meta-information piece regarding the second image data piece, and a display control unit configured to determine a superimposition style corresponding to a combination of the first and second meta-information pieces based on the first and second meta-information pieces and display a superimposition image of the first and second image data pieces in the superimposition style on a display unit.

Further features of the present invention will become apparent from the following description of exemplary embodiments with reference to the attached drawings.

BRIEF DESCRIPTION OF DRAWINGS

FIG. 5 illustrates a display screen on a display unit according to the first embodiment.

FIG. 6 is a table illustrating a relationship between image type combinations and display images according to the first embodiment.

FIG. 7 is a table illustrating a relationship between image type combinations and superimposition styles according to the first embodiment.

FIG. 8 illustrates a layout example of display regions on the display unit according to the first embodiment.

FIG. 9 illustrates a display screen on a display unit according to EXAMPLE 5.

FIG. 12 illustrates a notification message according to a sixth example.

FIG. 13 illustrates a display screen example on a display unit according to EXAMPLE 7.

FIG. 14 illustrates explanatory notes according to EXAMPLE 7.

FIG. 15 illustrates a display screen on a display unit according to EXAMPLE 7.

FIG. 16 illustrates a display screen on a display unit according to EXAMPLE 7.

DESCRIPTION OF EMBODIMENTS

Figure 1:
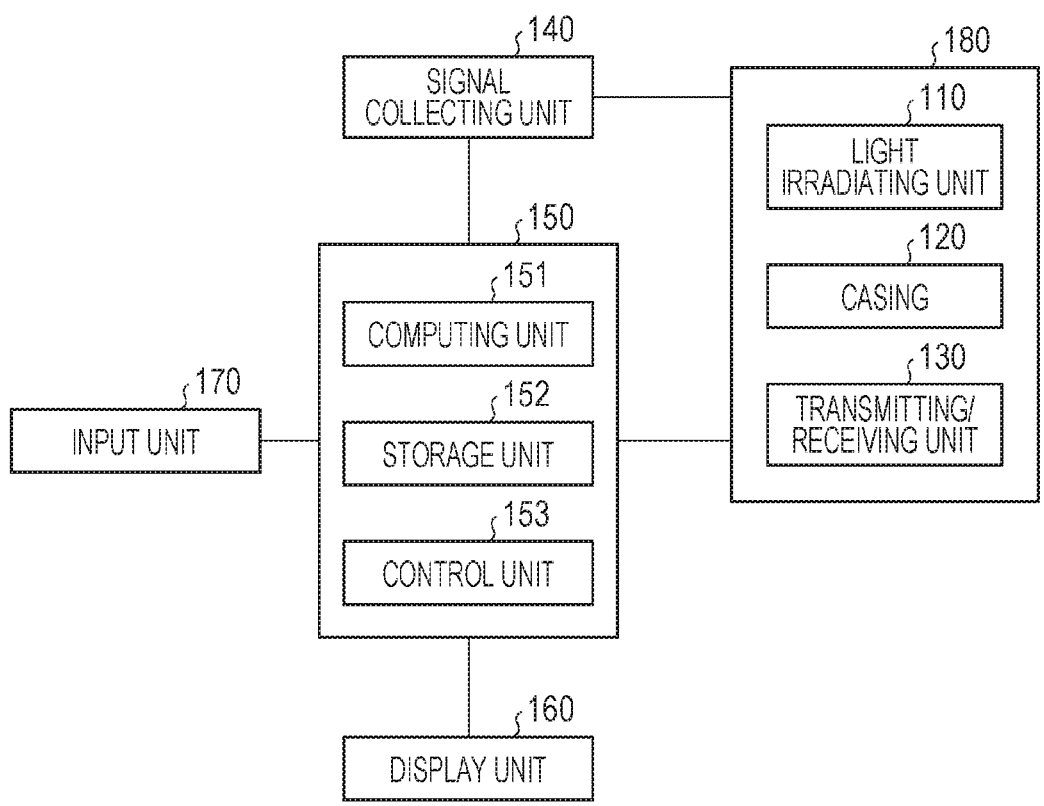
FIG. 1 is a schematic diagram illustrating a configuration of an image display system according to a first embodiment.

The present invention may determine a superimposition style based on meta-information regarding image data in order to display a superimposition image of a plurality of image data pieces. In other words, the present invention may determine a superimposition style based on a combination of meta-information pieces regarding a plurality of image data pieces. Here, the term "image type" refers to a type of an image data piece, that is, a difference in meaning between image values included in image data pieces.

For example, image types in an ultrasonic diagnostic apparatus may include B mode, doppler, and elastography, for example. In other words, image data pieces of a plurality of image types can be generated from one modality.

Image types in a photoacoustic diagnosis apparatus may include an initial sound pressure, an optical absorption coefficient, a total hemoglobin amount, and an oxygen saturation, for example.

For convenience of description, an acoustic wave generated by thermal expansion of an optical absorber irradiated with light will be called a photoacoustic wave, hereinafter. Furthermore, for convenience of description, an acoustic wave or a reflected wave (echo) transmitted from a transducer will be called an ultrasonic wave, hereinafter.

Additionally, an image type is allocated to each medical image data piece which is obtained from a modality such as a CT, an MRI and a PET.

In a medical field, DICOM (Digital Imaging and COmmunication in Medicine) is a standard that defines a medical image format widely used in applications for interpretation and diagnosis, for example, and a communication protocol between medical image apparatuses for such images.

For a DICOM data file, apparatus information and information regarding a patient ID and other image files corresponding to the image file can be held in detail as meta-information. For example, information regarding various types of medical apparatus images such as an X ray image and an ultrasound image can be saved. Thus, information pieces captured by different medical apparatuses can be used for interpretation and diagnosis by one image display system based on the DICOM standard.

According to the present invention, information representing an image type may be held in a tag of a DICOM data file so that the information representing the image type can be associated with the corresponding image data piece. Also according to the present invention, a character string representing an image type may be held in a file name of a DICOM data file so that the information representing the image type can be associated with the image data piece.

Such meta-information to be associated with image data piece may include information regarding a captured time such as an Instance Creation Date included in a general DICOM tag. The meta-information to be associated with an image data piece may include information regarding an image capture apparatus such as a modality. The meta-information to be associated with an image data piece may include information regarding an object such as a patient ID. The meta-information to be associated with an image data piece may include items for nesting elements such as an image region and an image data unit relating to the image data piece. The meta-information to be associated with an image data piece may include information representing a color map, a transmittance and a luminance range of a display image. The meta-information to be associated with an image data piece may include information representing image types which can be superimposed between DICOM data files of a plurality of image types, superimposed order (superimposing order) of image data pieces, and number of frames of images to be superimposed. Any other information relating to image data can be associated as meta-information.

Figure 23:
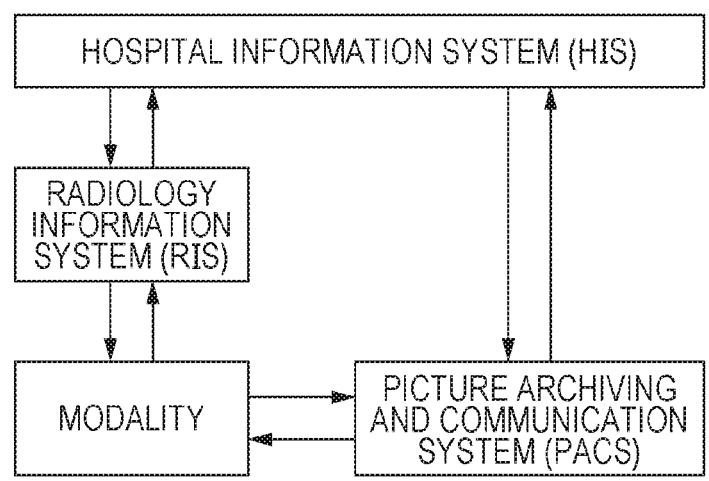
FIG. 23 illustrates a dataflow among an HIS, an RIS, a modality, and a PACS.

FIG. 23 is a schematic diagram illustrating a dataflow of medical information within a typical hospital. Here, a hospital information system (HIS) handles information in a hospital, such as an automatic reception system and an electronic record system. A radiology information system (RIS) manages reservations for inspections and treatments with a medical apparatus, patient information, and inspection information. A picture archiving and communication system (PACS) receives a DICOM file from a modality and saves it in a database. The term "PACS" refers to a server and its system which can search and transfer a DICOM file in response to a request from a display application. Referring to FIG. 23, information communication indicated by arrows and image data are based on the DICOM standard.

The term "DICOM" is a name of a standard that defines a medical image format and a communication protocol between medical image apparatuses. A DICOM file is a file including a combination of meta-information and image data based on DICOM herein. A DICOM image represents information held in an image data part of a DICOM file. The term "DICOM communication" refers to a communication to be performed based on the DICOM standard.

A DICOM file is generally an image file to be generated when an image of a patient is captured by a modality and is transmitted from the modality and is saved to a PACS server. A DICOM file generated by a modality may directly be transmitted to and be saved in a memory in a control apparatus such as a PC having a display application, without transmitting to the PACS server.

The modality may be a medical apparatus which can generate and communicate a DICOM file or an image processing application which is included in a medical apparatus or a PC and which can generate a DICOM file. A medical apparatus configured to generate a DICOM file may be an existing modality or a new modality. The existing modality may be an ultrasonic diagnostic apparatus configured to generate a B mode image or a doppler image, for example, an MRI (magnetic resonance imaging apparatus) configured to generate a T1 emphasized image or a T2 emphasized image, for example, an X ray diagnosis apparatus, SPECT, or a PET, for example. The new modality may be a photoacoustic diagnosis apparatus configured to detect photoacoustic waves generated from irradiated laser for imaging.

The modality can be connected to a PACS server or a PC via a cable, for example. When image capturing is performed by using a modality, a DICOM file may automatically be transmitted from the modality to the PACS server or the PC, or an operator may select a directory stored in the modality to save the DICOM file.

Meta-information saved in association with a medical image data piece obtained by such a modality may be held as a private tag of the DICOM file or may be standardized.

An image data piece generated based on DICOM will be described hereinafter, but any image data piece may be generated in any format, without limiting to DICOM.

Display control according to the present invention is applicable to a display application running on an image display system integrated to a modality (as described according to a first embodiment). The display control according to the present invention is applicable to a display application usable for viewing image data saved in a server in a PACS (as will be described according to a third embodiment).

The display control according to the present invention may determine a display layout based on a combination of meta-information pieces regarding a plurality of image data pieces (as will be described according to a second embodiment).

The display control according to the present invention may be configured to not only display a superimposition image based on two image data pieces but also display a superimposition image based on three or more image data pieces.

Embodiments of the present invention will be described with reference to drawings. Like numbers refer to like constituent elements throughout in principle, and any repetitive descriptions will be omitted.

First Embodiment

A configuration of and processing in an image display system according to a first embodiment will be described below.

According to the first embodiment, an operator may select two DICOM files on a file selection screen for a DICOM image. According to this embodiment, a superimposition style appropriate for the two selected DICOM files is determined based on information described in a tag of a DICOM file such as information representing an image type. According to this embodiment, at least one of superimposition styles of a display color map (color scheme), superimposed order (superimposing order), a transmittance, and a luminance range is determined based on a combination of a plurality of image types of DICOM files. Based on the determined superimposition style, the images of the selected two DICOM files are superimposed for display.

Under a display control according to this embodiment, a superimposition style appropriate for diagnosis can be set in a display application even when an operator does not know a superimposition style appropriate for the image type of DICOM files. When an operator knows a superimposition style for an image type, superimposition processing appropriate for diagnosis is performed in the display application, which can simplify an operation of the operator for displaying an appropriate superimposition image.

According to this embodiment, a photoacoustic diagnosis apparatus and an ultrasonic diagnostic apparatus are used as modalities. With reference to FIG. 1, a configuration of an image display system according to this embodiment will be described. FIG. 1 is a schematic block diagram illustrating an overall image display system. The image display system according to this embodiment includes a signal collecting unit 140, a computer 150, a display unit 160 an input unit 170, and a probe 180. Parts of the signal collecting unit 140, the probe 180, and the computer 150 may function as a modality for generating image data of a DICOM file.

Figure 2:
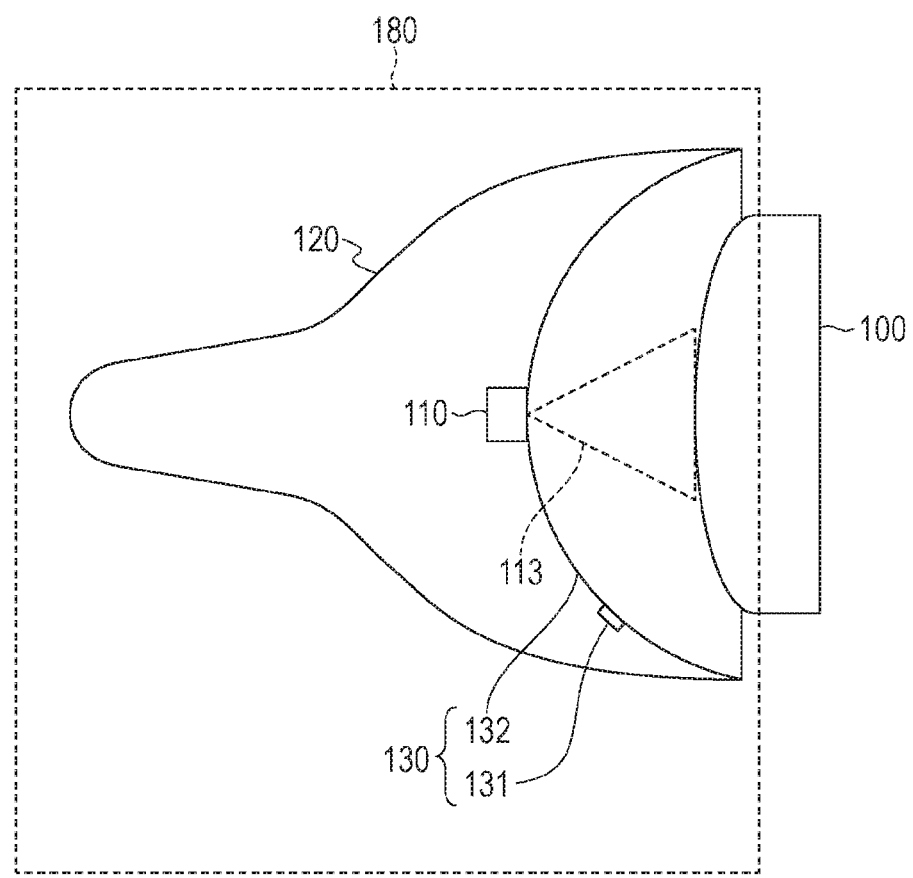
FIG. 2 is a schematic diagram of a probe according to the first embodiment.

FIG. 2 is a schematic diagram of the probe 180 according to this embodiment. The probe 180 has a light irradiating unit 110, a casing 120 including a holding portion, and a transmitting/receiving unit 130. An object 100 is a measurement object.

The light irradiating unit 110 irradiates pulsed light 113 to the object 100 so that acoustic waves can occur within the object 100. An acoustic wave caused by light due to a photoacoustic effect will also be called a photoacoustic wave. The transmitting/receiving unit 130 is configured to receive photoacoustic waves and output an analog electric signal (photoacoustic signal). The transmitting/receiving unit 130 is further configured to transmit ultrasonic waves to the object 100 and receive echo waves of the transmitted ultrasonic waves to output an analog electric signal (ultrasonic signal).

The signal collecting unit 140 is configured to convert an analog signal output from the transmitting/receiving unit 130 to a digital signal and output it to the computer 150. The computer 150 stores the digital signal output from the signal collecting unit 140 as signal data derived from ultrasonic waves or photoacoustic waves.

The computer 150 is configured to perform signal processing on a stored digital signal to generate image data representing an ultrasound image or a photoacoustic image. The computer 150 performs an image process on the resulting image data and then outputs image data to the display unit 160. The display unit 160 is configured to display an ultrasound image or a photoacoustic image. A doctor or a technician as an operator can perform diagnosis by checking an ultrasound image and a photoacoustic image displayed on the display unit 160. A display image is saved in a data management system connected to a memory within the computer 150 or to the modality over a network based on a save instruction from an operator or the computer 150.

The computer 150 is configured to perform drive control over components included in the image display system. The display unit 160 may display an image generated in the computer 150 and a GUI. The input unit 170 is configured to be usable by an operator for inputting information. An operator may use the input unit 170 to perform an operation such as instructing to save a display image.

A photoacoustic image obtained by the image display system according to this embodiment is a concept including an image derived from photoacoustic waves generated from irradiated light. A photoacoustic image includes image data representing at least one spatial distribution of information regarding sound pressure for generating photoacoustic waves (initial sound pressure), an optical absorption energy density, an optical absorption coefficient, and a concentration of a substance contained in an object, for example. The information regarding a concentration of a substance may be an oxyhemoglobin concentration, a deoxyhemoglobin concentration, a total hemoglobin amount, or an oxygen saturation, for example. The total hemoglobin amount is a sum of an oxyhemoglobin amount and a deoxyhemoglobin amount. The oxygen saturation is a ratio of oxyhemoglobin to whole hemoglobin. The photoacoustic image is not limited to an image representing a spatial distribution but may be an image representing a numerical value or text. For example, the photoacoustic image is a concept including an image representing information derived from a photoacoustic signal, such as a photoacoustic signal (RAW data), an average concentration of a substance contained in an object, a pixel value at a specific position in a spatial distribution, or a statistic (such as an average value or a median value) of pixel values in a spatial distribution, for example. As a photoacoustic image, a numerical value of an average concentration of a substance contained in an object, for example, may be displayed on the display unit 160.

An ultrasound image obtained by the image display system according to this embodiment includes image data of at least one of a B mode image, a doppler image, and an elastography image. The ultrasound image is a concept including an image obtained by transmitting and receiving ultrasonic waves.

Components of an object information obtaining apparatus according to this embodiment will be described in detail below.

Light Irradiating Unit 110

The light irradiating unit 110 includes a light source configured to emit pulsed light 113, and an optical system configured to guide the pulsed light 113 emitted from the light source to the object 100. The pulsed light here includes so-called square-wave or triangle-wave light.

The light emitted from the light source may have a pulse width ranging from 1 ns to 100 ns. The light may have a wavelength ranging from 400 nm to 1600 nm. In order to image a blood vessel neighboring to a surface of a living body with a high resolution, light having a wavelength (ranging from 400 nm to 700 nm) which is largely absorbed by a blood vessel may be used. On the other hand, in order to image a deep part of a living body, light having a wavelength (ranging from 700 nm to 1100 nm) which is typically absorbed less by background tissue (such as water or fat) of a living body may be used.

The light source may be a laser or a light emitting diode, for example. Alternatively, the light source may be capable of performing wavelength conversion for measurement using light having a plurality of wavelengths. When light having a plurality of wavelengths is irradiated to an object, a plurality of light sources which emit light beams having wavelengths different from each other may be provided so that the light beams can be irradiated alternately from the light sources. A set of a plurality of light sources if used is also collectively called as a light source. Various lasers may be applied here such as a solid-state laser, a gas laser, a dye laser, and a semiconductor laser. For example, a pulsed laser such as an Nd:YAG laser and an alexandrite laser may be used as the light source 111. Alternatively, a Ti:sa laser or an OPO (Optical Parametric Oscillators) laser applying an Nd:YAG laser light as excited light may be used as the light source. A microwave source may be used as the light source instead.

The optical system may include optical elements such as a lens, a mirror, and optical fiber. In a case where a breast is the object 100, for example, pulsed light having an increased beam diameter is to be irradiated. Accordingly, the optical system may include a light emitting unit having a diffusing plate configured to diffuse light. On the other hand, an photoacoustic microscope may have an increased resolution with an optical system having a light emitting unit including a lens to irradiate a focused beam.

Alternatively, the pulsed light 113 may be irradiated from the light source directly to the object 100 by the light irradiating unit 110 without an optical system. The components of the light irradiating unit 110 such as the light source may be provided externally to the casing 120.

Transmitting/Receiving Unit 130

The transmitting/receiving unit 130 includes a transducer 131 configured to output an electric signal from received acoustic waves, and a supporting member 132 configured to support the transducer 131. The transducer 131 is also capable of transmitting acoustic waves. FIG. 2 only illustrates one transducer 131 for simplicity, the transmitting/receiving unit 130 may include a plurality of transducers.

The transducer 131 may be formed of a piezoelectric ceramic material such as PZT (lead zirconate titanate) or a polymer piezoelectric film material such as PVDF (polyvinylidene difluoride), for example. An element excluding a piezoelectric element may be used instead. For example, capacitive micro-machined ultrasonic transducers, CMUT, or a transducer applying a Fabry-Perot interferometer may be used. Any kind of transducer may be adopted if it is capable of outputting an electric signal from received acoustic waves. A signal obtained by the transducer is a temporal resolution signal. In other words, a signal obtained by a receiving element has an amplitude representing a value (such as a value proportional to sound pressure) based on sound pressure received by the transducer at different times.

Photoacoustic waves contain frequency components typically ranging from 100 KHz to 100 MHz, and the transducer 131 is capable of detecting these frequencies.

The supporting member 132 may be formed of a metallic material having a high mechanical strength. For a case where an operator holds the casing 120 to scan the probe 180, the supporting member 132 may be formed of a polymer material such as plastics from view point of weight reduction. In order to launch more irradiation light into an object, the supporting member 132 may have a mirror surface or a surface processed to be light scattering closer to the object 100. According to this embodiment, the supporting member 132 has a hemispherical enclosure shape and is configured to support a plurality of transducers 131 on the hemispherical enclosure. In this case, the transducers 131 arranged on the supporting member 132 have directional axes gathering closely to the center of the curvature of the hemisphere. An image obtained by using a group of electric signals output from the plurality of transducers 131 has high image quality at a part produced by electric signals from the transducers around the center of curvature. The supporting member 132 may have any configuration if it can support the transducers 131. The supporting member 132 may have a plurality of transducers on its plane or curved surface such as a 1D array, a 1.5D array, a 1.75D array, and a 2D array.

The supporting member 132 may function as a container configured to reserve an acoustic matching material. In other words, the supporting member 132 may be a container for arranging an acoustic matching material between the transducer 131 and the object 100.

The transmitting/receiving unit 130 may include an amplifier configured to amplify time-series analog signals output from the transducers 131. The transmitting/receiving unit 130 may include an A/D converter configured to convert time-series analog signals output from the transducers 131 to time-series digital signals. In other words, the transmitting/receiving unit 130 may include a signal collecting unit 140, which will be described below.

For detection of acoustic waves at various angles, the transducer 131 may be arranged to surround the entire perimeter of the object 100. However, in a case where it is difficult to arrange transducers to surround the entire perimeter of the object 100, the transducers may be arranged on the hemisphere supporting member to surround the entire perimeter as illustrated in FIG. 2.

The arrangement and number of transducers and the shape of the supporting member may be optimized in accordance with an object, and any kind of transmitting/receiving unit 130 may be adopted with respect to the present invention.

The space between the transmitting/receiving unit 130 and the object 100 is filled with a medium in which photoacoustic waves can propagate. The medium may be made of a material in which acoustic waves can propagate and which has an acoustic characteristic matching at an interface between the object 100 and the transducer 131 and has a transmittance of photoacoustic waves as high as possible. For example, the medium may be water or ultrasound gel.

It should be noted that a transducer configured to transmit ultrasonic waves and a transducer configured to receive acoustic waves may be provided separately. Alternatively, one transducer may be provided which is configured to transmit ultrasonic waves and receive acoustic waves. A transducer configured to transmit and receive ultrasonic waves and a transducer configured to receive photoacoustic waves may be provided separately. Alternatively, one transducer may be provided which is configured to transmit and receive ultrasonic waves and receive photoacoustic waves.

Signal Collecting Unit 140

The signal collecting unit 140 includes an amplifier configured to amplify an electric signal being an analog signal output from the transducer 131 and an A/D converter configured to convert an analog signal output from the amplifier to a digital signal. The signal collecting unit 140 may be an FPGA (Field Programmable Gate Array) chip, for example. A digital signal output from the signal collecting unit 140 is stored in a storage unit 152 within the computer 150. The signal collecting unit 140 is also called a Data Acquisition System (DAS). The term "electric signal" herein refers to a concept including an analog signal and a digital signal. The signal collecting unit 140 is connected to a light detection sensor attached to the light emitting unit in the light irradiating unit 110 and may start processing by being triggered by and synchronized with emission of the pulsed light 113 from the light irradiating unit 110. The signal collecting unit 140 may start the processing by being triggered by and synchronized with an instruction given by using a freeze button.

Computer 150

The computer 150 includes a computing unit 151, the storage unit 152, and a control unit 153. These components have functions, which will be described with reference to a processing flow.

A unit responsible for a computing function as the computing unit 151 may have a processor such as a CPU and a GPU (Graphics Processing Unit) and a computing circuit such as an FPGA (Field Programmable Gate Array) chip. These units may include a plurality of processors and computing circuits, instead of a single processor and a single computing circuit. The computing unit 151 may process a reception signal in accordance with parameters such as the speed of sound of an object and a holding cup from the input unit 170.

The storage unit 152 may be a non-transitory storage medium such as a ROM (Read only memory), a magnetic disk and a flash memory. The storage unit 152 may be a volatile medium such as a RAM (Random Access Memory). A storage medium storing a program is a non-transitory storage medium. The storage unit 152 may include a plurality of storage media without limiting to one storage medium.

The storage unit 152 can save image data representing an ultrasonic wave image or a photoacoustic image, for example, generated by the computing unit 151 by applying a method, which will be described below. The storage unit 152 may save an image obtained by a modality apparatus different from the image display system according to this embodiment.

The control unit 153 is configured by a computing element such as a CPU. The control unit 153 is configured to control operations performed by components of the photoacoustic apparatus. The control unit 153 may control the components of the inspection system in response to an instruction signal based on an operation such as a start of measurement given through the input unit 170. The control unit 153 may read out program code stored in the storage unit 152 and controls an operation performed by a component of the inspection system.

The computer 150 may be a specially designed workstation. The components of the computer 150 may be configured by different hardware modules. Alternatively, at least partial components of the computer 150 may be configured by a single hardware module.

Figure 3:
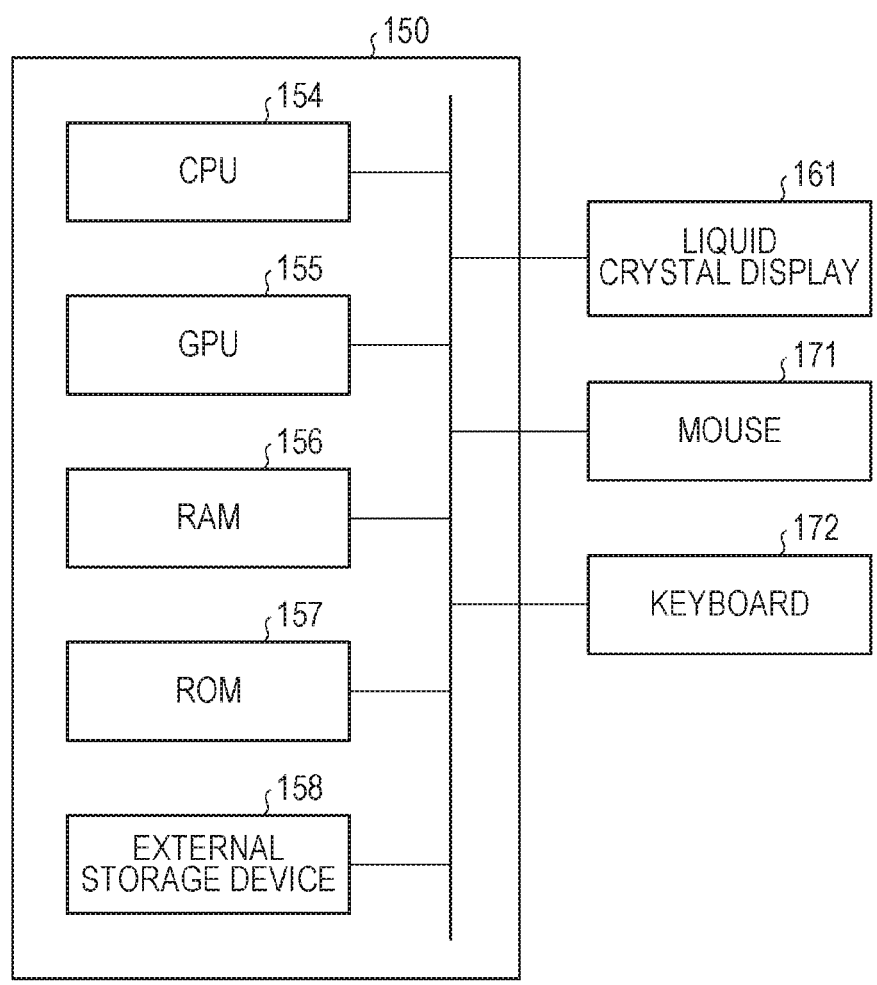
FIG. 3 is a configuration diagram illustrating a computer and peripherals therefor according to the first embodiment.

FIG. 3 illustrates a specific configuration example of the computer 150 according to this embodiment. The computer 150 according to this embodiment includes a CPU 154, a GPU 155, a RAM 156, a ROM 157, and an external storage device 158. A liquid crystal display 161 as the display unit 160 and a mouse 171 and a keyboard 172 as the input unit 170 are connected to the computer 150.

The computer 150 and the plurality of transducers 131 may be accommodated in a common casing. Alternatively, partial signal processing may be performed by the computer accommodated in the casing while the rest of the signal processing may be performed by a computer provided externally to the casing. In this case, the computers provided internally and externally to the casing may be collectively called a computer according to this embodiment.

Display Unit 160

The display unit 160 is a display such as a liquid crystal display and an organic EL (Electro Luminescence). The display unit 160 is configured to display an image based on object information obtained by the computer 150 and a numerical value corresponding to a specific position therein. The display unit 160 may display a graphical user interface (GUI) usable for operating an image or the system. For display of object information, the display unit 160 or the computer 150 may perform an image process (such as adjustment of a luminance value) thereon.

Input Unit 170

The input unit 170 may be an operating console which can be operated by a user and may include a mouse and a keyboard. The display unit 160 may include a touch panel so that the display unit 160 can also be used as the input unit 170. The input unit 170 may include a freeze button usable by a user for giving an instruction such as a save instruction, which will be described below.

The components of the image display system may be provided as separate apparatuses or may be integrated to one system. Alternatively, at least partial components of the image display system may be integrated to one apparatus.

Object 100

The object 100 will be described below though it is not a component of the image display system. The image display system according to this embodiment is usable for purposes such as diagnoses of human or animal malignant tumors and blood vessel diseases and follow-ups of chemical treatments. Therefore, the object 100 is assumed as a region to be diagnosed such as a living body, more specifically, the limbs including the breast, the neck, the abdomen, organs, a vascular network, the head, a finger and a toe of a human body or an animal. For example, in a case where a human body is a measurement object, oxyhemoglobin or deoxyhemoglobin or a blood vessel mostly including them or a neovessel formed in neighborhood of a tumor may be an optical absorber. Plaque of a carotid artery wall may be an optical absorber. Alternatively, a pigment such as methylene blue (MB), indocyanine green (ICG), gold minute particles, or an externally introduced substance integrating or chemically modifying them may be an optical absorber.

Image Generation Flow

The probe 180 may transmit and receive ultrasonic waves from the object 100 to output an ultrasonic signal. The signal collecting unit 140 may perform AD conversion processing on the ultrasonic signal and transmit the processed ultrasonic signal to the computer 150. The ultrasonic signal being a digital signal is stored in a storage unit 152. The computing unit 151 performs re-construction processing such as phasing addition (Delay and Sum) on an ultrasonic signal to generate an ultrasound image. The ultrasonic signal saved in the storage unit 152 may be deleted after the ultrasonic wave image is generated therefrom. First, the control unit 153 transmits information (control signal) representing light irradiation to the probe 180. The probe 180 receiving the information representing light irradiation irradiates light to the object 100, receives photoacoustic waves generated due to the light irradiation and outputs a photoacoustic signal. The signal collecting unit 140 performs AD conversion processing on the photoacoustic signal and transmits the processed photoacoustic signal to the computer 150. The photoacoustic signal being a digital signal is stored in the storage unit 152. The computing unit 151 performs reconstruction processing such as Universal BackProjection (UBP) on the photoacoustic signal to generate a photoacoustic image. The photoacoustic signal saved in the storage unit 152 may be deleted after the photoacoustic image is generated.

Display Control Flow

According to this embodiment, the control unit 153 performs the following display control. That is, operations of the following display application are controlled by the control unit 153.

First, when an operator uses the input unit 170 to give an activation instruction, the control unit 153 activates a display application.

Figure 4:
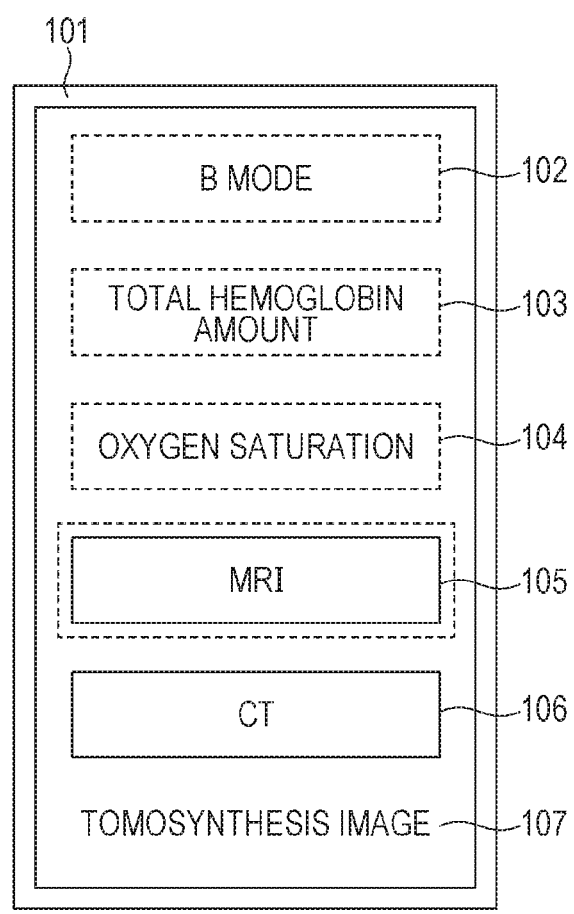
FIG. 4 illustrates a file selection window according to the first embodiment.

Next, a selection screen for a DICOM file to be displayed is displayed on the display unit 160. The selection screen may be displayed by performing a mode selection operation in the display application. For example, an operator may select a DICOM file selection button in the display application so that a DICOM file storage directory is displayed in a user interface. Next, an operator may select a DICOM file to be displayed in the user interface. The control unit 153 may obtain meta-information regarding an image type saved in association with the DICOM file, identify DICOM files being image types to be combined suitably for being superimposed, and display the combination of the DICOM files appropriate for being superimposed such that they can be identified. FIG. 4 illustrates an example selection screen for DICOM files. A file name may be enclosed by a colored broken line or solid line, for example, as illustrated in FIG. 4, or may brink for emphasized display such that an operator can identify a combination of image types appropriate for superimposition. FIG. 4 illustrates a selection window 101 for selecting a DICOM file in the display application. The selection window 101 displays icons 102 to 107 for image data pieces representing DICOM files. The DICOM files for image types corresponding to the icons 102 to 105 correspond to a combination of DICOM files appropriate for superimposition and are indicated by broken lines. The DICOM files of image types corresponding to the icons 105 and 106 correspond to a combination appropriate for superimposition and are indicated by a solid line. The DICOM file of the image type corresponding to the icon 107 is not appropriate for superimposition with any file and is not emphasized with a line. Having described the example in which the appropriateness for superimposition of a file is indicated by an enclosing line, the appropriateness for superimposition may be indicated in any manner. Having described the example using icons as items representing image types of image data pieces, the image types may be represented by any other items. For example, an image type may be identified based on an item such as a list box containing image types of image data pieces.

The control unit 153 may determine the appropriateness for superimposition based on a combination of image types associated with image data pieces. The control unit 153 may determine whether the combination of image types to be superimposed is appropriate for the superimposition or not with reference to a table illustrating a relationship between combination of image types and appropriateness of superimpositions. An image data piece may be associated with information representing an image type that is appropriate for superimposition with the image data piece. In this case, the control unit 153 may determine whether the combination of target image data pieces is appropriate for superimposition based on the information, and the determination result may be notified to a notification unit such as the display unit 160. The notification unit may provide a visual indication or an audio notification.

The control unit 153 may determine the appropriateness for superimposition of image data pieces based on a synchronization method for obtaining the images or the captured times. For example, the control unit 153 may determine image data pieces based on a same synchronization method or image data pieces captured at neighboring times as a combination appropriate for superimposition.

The control unit 153 may further determine appropriateness for superimposition based on patient IDs associated with image data pieces. The patient IDs may be IDs allocated to patients whose images are captured by a medical apparatus. For example, the control unit 153 may determine that images with an identical patient ID are appropriate for superimposition and may determine that images having different patient IDs are not appropriate for superimposition. Different patient IDs may possibly be associated with an identical patient when images of the patient have been captured in a plurality of hospitals. In this case, different patient IDs may be associated with an identical patient so that image data pieces having the different patient IDs may be determined as image data pieces of the identical patient and as being appropriate for superimposition.

Next, an operator may select a plurality of DICOM files to be superimposed for display by using a cursor. According to this embodiment, a user interface example for selecting image data pieces will be described with reference to FIG. 5. FIG. 5 illustrates an example in which a B mode image and a total hemoglobin amount image are selected. A pop-up window 206 for selecting DICOM files appears when the display application is activated to select files. A DICOM files group 207 includes a DICOM files of the currently selected B mode image and total hemoglobin amount image, which are emphasized with thick lines for display. An image display region 208 is in an image viewer of the image display application. An operator may drag and drop a target file from the image data group 207 to the image display region 208 by using the input unit 170 so that the file can be available for superimposition on the viewer. Drag-and-drop operations to be performed on the selected files are indicated by arrows 209. A plurality of selected files may collectively be dragged and dropped to the image display region 208 by using a displayed cursor, for example, for superimposing them. Files may be dragged and dropped to the image display region 208 one by one to superimpose them. A file to be read may be selected by pressing a file reading button in a selection list which appears in response to a right click on a selected file. When files are dragged and dropped to a region other than the image display region 208, it may be determined that an image is selected, and a superimposition image of selected target DICOM files may be displayed. Any method is applicable if an operator can select image data pieces to be superimposed.

The control unit 153 may read out meta-information such as an image type saved in association with a DICOM file dropped in the image display region 208 and may set a superimposition style based on a combination of meta-information pieces of the dropped DICOM files. The control unit 153 may set a superimposition style corresponding to a combination of meta-information pieces regarding a plurality of image data pieces with reference to information (reference information) representing a relationship of combinations of meta-information pieces and superimposition style.

FIGS. 6 and 7 are table examples illustrating information representing relationships between combinations of image types and superimposition styles. Leftmost columns in FIGS. 6 and 7 illustrate numbers representing variations of combinations of image types.

FIG. 6 is a table illustrating which display image is to be displayed for each of combinations of image types. For example, when image types of B mode and total hemoglobin amount are selected, a display image 1 and a display image 2 are displayed, which corresponds to a combination No. 1.

FIG. 7 illustrates a superimposition style for display images to be displayed for each of combinations of image types. For example, FIG. 7 illustrates that a gray-scale B mode image is displayed as a display image 1 on a display region corresponding to (1,1) in the display unit 160 for the combination No. 1. FIG. 7 illustrates that, for the combination No. 1, a display image 2 in which a B mode image (base image) and a total hemoglobin amount image are sequentially superimposed is also displayed on a display region corresponding to (1,2) in the display unit 160. FIG. 7 further illustrates that the B mode image included in the display image 2 is displayed in a gray-scale and that the total hemoglobin amount image therein is displayed in a yellow color scale. Thus, the control unit 153 can determine a superimposition style based on a combination of image types. FIG. 8 illustrates a layout example of display regions in the display unit 160 where display regions illustrated in FIG. 7 correspond to display regions (1,1) to (2,3) in the display unit 160 illustrated in FIG. 8.

An operator may use the input unit 170 to change a parameter for a superimposition style corresponding to a combination of image types.

The control unit 153 may determine whether selected DICOM files are appropriate to be superimposed or not by the method as described above and may notify the result to the operator by using a notification unit.

Display parameters not illustrated in the table in FIG. 7 may be set based on meta-information associated with an image data piece. For example, because FIG. 7 does not illustrate transmittances and luminance ranges, the display parameters may be set based on information regarding a transmittance and a luminance range associated with an image data piece.

The transmittance is a value of a proportion set for the transmittance of color of a color map to be displayed in one or more image data pieces of images to be superimposed. The displaying according to this embodiment is set to display a B mode image with a transmittance of 0% and displays a total hemoglobin amount image thereon with a transmittance set as required for superimposition. In other words, a transmittance of at least an image to be arranged in the foreground is set as required for superimposition.

In a case where a total hemoglobin amount image H is a two-dimensional image, the transmittance T(i,j)(%) at a pixel at H(i,j) can be calculated by the following expression (1).

$$T(i, j) = 100 - \frac{H(i, j) - \min H}{\max H - \min H} \times 100 \quad (1)$$

where min H is a minimum value of H(i,j), max H is a maximum value of H(i,j), and the second term on the right side of Expression (1) normalizes the intensity of H(i,j) to 100. The value may be subtracted from 100 to calculate the transmittance. In other words, at a pixel having the highest intensity with H(i,j), T(i,j) is equal to 0% and is displayed in a color in the color map corresponding to the value of the total hemoglobin amount. Though the transmittance is normalized by using the maximum value and the minimum value of the hemoglobin amount, the transmittance is equal to 0% when a maximum pixel value exists in the entire image, preventing the image to be superimposed from being viewed. Therefore, the transmittance is not to be calculated in a range from 0% to 100%. The transmittance may be calculated in a range from a minimum transmittance of 20% to a maximum transmittance of 100% so that the image to be superimposed can be viewed therethrough.

The control unit 153 may read out an expression representing a transmittance associated with an image data piece and may calculate the transmittance for each of pixels and voxels. The control unit 153 may read out information regarding transmittances of all pixels and voxels associated with image data.

The luminance ranges from a maximum value to a minimum value of the intensities of an image data piece. Based on the luminance range, display colors, transmittances and a window level are set for the image intensity in display.

A term "captured time" refers to a clock time when an image is captured. There may be DICOM files of a plurality of types captured at a plurality of captured times. In this case, DICOM images captured at different clock times or captured at substantially equal captured times may sometimes be superimposed for comparison. In this case, the tag may have information (such as a name and a UID) regarding a DICOM image captured at a captured time to be superimposed for display so that DICOM images at a plurality of captured times can be superimposed based on their captured times for display.

A term "the number of slices" refers to the number of slices of a DICOM file, and there are a single-frame DICOM file having one frame and a multiframe DICOM file having a plurality of slices. A term "slice interval" refers to an interval between a plurality of slices. In order to superimpose two multiframe DICOM files, all corresponding slices may be superimposed for display if they have equal intervals between slices and an equal number of slices. However, when DICOM files having different number of slices and different slice intervals are to be superimposed, different slices of one DICOM file cannot be allocated to all of slices of the other DICOM file. In this case, a slice of the other DICOM image at nearest neighboring coordinates may be allocated to coordinates (slice position slice in a directional axis of an increase in number of slices) of a slice of the one DICOM image to be superimposed for display. Alternatively, a slice corresponding to coordinates of a slice of one DICOM image to be superimposed may be generated by interpolating from a plurality of slices of the other DICOM image at neighboring coordinates of the coordinate position. The pixel intensity of an image at a certain position of the slice acquired by the interpolation may be the pixel intensity of the image at the corresponding position of at least one other spatially neighboring slice.

When a plurality of multiframe DICOM images is to be displayed in a plurality of image display regions on a viewer by displaying each slice in synchronism, the synchronization display may be based on the slice width of a slice having a minimum slice width. In this case, when the slice displayed in one DICOM image is not matched in position with the slice of the other DICOM image, a process may be performed to display a nearest neighboring slice, for example, or the matched slice may be acquired by interpolation from neighboring slices.

Irrespective of single frame and multiframe DICOM files, data included in meta-information other than the image data parts of DICOM files may be used to generate a superimposition image in one DICOM file. For example, when an image data part of a DICOM file holds an oxygen saturation image and when total hemoglobin amount data corresponding to pixels and voxels of the oxygen saturation image is held in the tag, images can be superimposed without preparing a plurality of DICOM files. Also in this case, information representing the image type (total hemoglobin amount in this case) of image data pieces held in the tag may be stored in association. For example, an image data part of a DICOM file may hold an oxygen saturation image, and a mask image allocating 1 or 0 to each of pixels or voxels may be held in a tag thereof. In this case, the mask image may be read out from the tag, and the mask image may be used to mask the oxygen saturation image held in the image data part for display thereafter.

In order to synchronize or superimpose multiframe DICOM images of different image types for display, states of two DICOM images to be superimposed may be matched as much as possible before they are displayed. In other words, in order to synchronize and superimpose images held having different states such as different orientations or sizes, the orientation or size of at least one of the images may be converted three-dimensionally for deformation and positioning before the superimposition display. In this case, the deformation conditions may be associated with the superimposition image to be held.

The control unit 153 may read a plurality of DICOM files and their meta-information pieces and may set a layout on the display unit 160 in accordance with a combination of meta-information pieces. Layouts displayable based on combinations of meta-information piece may be presented on a pop-up window by the display application, and an operator may select one from the presented layouts.

The control unit 153 may not superimpose a selected DICOM image. A superimposition image may not be generated on any of screens based on the layout selected by an operator even as a result of a drag and drop of a DICOM file performed by the operator. All of a plurality of selected files may simultaneously be dragged and dropped to a specific display region, or the selected files may be dragged and dropped one by one to a specific display region. Three different images may be superimposed for display.

The control unit 153 may automatically superimpose DICOM images that are captured at a matched time based on their meta-information pieces. The control unit 153 may superimpose for display a plurality of DICOM images of one type that are captured at different times and a plurality of DICOM images of another type that are captured at different times, based on their meta-information pieces. In this case, images having an object at an identical position or neighboring positions or images captured at a same time or at neighboring times may be superimposed for display. The control unit 153 may sequentially update and display on one screen a plurality of superimposition images captured at different times or may display them on a plurality of screens based on a lapse of time thereof.

An operator may use the input unit 170 to change a superimposition style set as a default.

Display parameters not including a superimposition style corresponding to a combination of image types may be determined based on meta-information piece saved associated with an image data piece, excluding an image type. For example, when a color scheme or superimposed order corresponding to a combination of image types is not provided, the control unit 153 may determine the color scheme or superimposed order based on information representing color schemes or superimposed order described in the tags of the target image data pieces.

A table describing display modes corresponding to image types may be provided so that image data pieces can be superimposed in a display mode corresponding to their image types. Thus, the superimposition image may be displayed in a superimposition style corresponding to a combination of the image types. For example, for images of an image type of doppler image, a display mode may be applied in which a blood flow moving toward a probe is displayed in red and a blood flow moving away from the probe is displayed in blue. For images of an image type of B mode image, the images may be superimposed in a gray-scale display mode. Setting a superimposition style in this manner may cause a problem in a resulting superimposition image, however. For example, when images are to be superimposed based on color map recommended with their image types and have similar color tones, it may be difficult to distinguish between the images, which may possibly hinder diagnosis. In this case, whether one of the image data pieces has a tag describing an acceptable color map is checked. If so and when the acceptable color map is an easily identifiable color map, the acceptable color map may be used. For example, a case will be described in which one DICOM image to be superimposed has a color map of red-green-blue corresponding to its image type, and the other DICOM image to be superimposed has a color map of blue-white-red corresponding to its image type. In this case, if the acceptable color map of one of them is based on a gray scale, the one color map may be displayed in a gray scale. If the color maps corresponding to the image types of the DICOM images are based on a gray scale and when an acceptable color map of one of them displays color excluding black and white, the color map may be applied for displaying the images. For achieving these display forms, a modality may save an image data piece in association with a meta-information piece representing an acceptable color map.

When one DICOM image has a color map of red-green-blue and the other DICOM image has a color map of blue-white-red, one of the color maps may be converted to monochrome or both of the color maps may be converted to a clearer color map for display. An image type not based on a generally used color map, a tag therefor may describe that there is no specific color map. In this case, a display application may set a color map so as to prevent confusion in interpretation with respect to the color map to be superimposed. An image may be displayed in one color, or a color map may be applied thereto in which color changes based on the intensities of the image. A relationship between color and image value represented by an expression may be held in a tag of an image data piece, and the control unit 153 may calculate and generate a color map based on the expression.

When images are superimposed on an image display region, the image types or details of the images may not be identified if the superimposition image is just displayed. Details of a displayed image may be displayed as explanatory notes near the image display region. Alternatively, a displayed image may be right-clicked or an information display button may be selected in a state the displayed image is being selected so that a pop-up window may appear to display details of the selected image.

The display method according to this embodiment can simplify an operation of an operator for setting display parameters for displaying an image appropriate for diagnosis.

Example 1

A specific example will be described below. According to EXAMPLE 1, a total hemoglobin amount image output from a photoacoustic diagnosis apparatus and a B mode image output from an ultrasonic diagnostic apparatus are displayed on a display unit by a display application. In this case, the total hemoglobin amount image is superimposed on the ultrasound B mode image where the B mode image is displayed in a gray-scale based on intensities of 0 to 255 while the total hemoglobin amount image is displayed in a color map based on yellow.

In this example, an operator first activates a display application in a PC, starts an image viewer, and presses a DICOM file selection button in the display application. When the operator presses the DICOM file selection button, a pop-up window being a selection screen appears, and the operator may select DICOM files to be displayed. According to this example, an operator selects a total hemoglobin amount DICOM file and a B mode image DICOM file and drags and drops them onto the viewer. When the two DICOM files are dropped, the control unit 153 reads out information representing image types described in the tags of the DICOM files. The control unit 153 obtains information regarding a color map, intensities, a transmittance, and the type name of the superimposition targets appropriate for interpretation and diagnosis corresponding to a combination of the read image types. The control unit 153 then sets information for superimposition, such as information regarding a color map, intensities, a transmittance, and the type name of the superimposition targets appropriate for interpretation and diagnosis corresponding to the image types and superimposes them.

According to this example, the display application sets the B mode image of a gray-scale based on intensities of 0 to 255 as a base image in a first layer (background) and sets the total hemoglobin amount image in a yellow color map in a second layer (foreground). The display application sets a transmittance based on the combination of the image type for the total hemoglobin amount image in the second layer and superimposes it on the B mode image in the first layer. The transmittance is increased for a lower total hemoglobin amount while the transmittance is reduced for a higher total hemoglobin amount so that a part having a higher amount of blood and a higher total hemoglobin amount can be displayed in yellow with a high intensity.

Thus, when an operator uses the display application to select a plurality of DICOM files to be displayed, the images can be displayed under a condition appropriate for interpretation and diagnosis based on information described in tags thereof.

Example 2

According to EXAMPLE 2, an oxygen saturation image output from a photoacoustic diagnosis apparatus and a B mode image output from an ultrasonic diagnostic apparatus are displayed on a display unit. In this case, the oxygen saturation image is superimposed on the B mode image where the B mode image is displayed in gray-scale based on intensities of 0 to 255 while the oxygen saturation image is displayed in a color map of blue to red.

In this example, an operator first activates a display application in a PC and presses a DICOM file selection button in the display application. When the operator presses the DICOM file selection button, a pop-up window being a selection screen appears, and the operator may select DICOM images to be displayed. According to this example, an operator selects an oxygen saturation DICOM file and a B mode image DICOM file. When the two DICOM files are selected, the control unit 153 reads out information representing image types described in the tags of the DICOM files. The control unit 153 obtains information regarding a color map, intensities, a transmittance, and the type name of the superimposition targets appropriate for interpretation and diagnosis corresponding to a combination of the image types. The control unit 153 then sets information for display, such as information regarding a color map, intensities, a transmittance, and the type name of the superimposition targets appropriate for interpretation and diagnosis corresponding to a combination of the image types and displays them.

According to this example, the B mode image is set in a first layer to display it in a gray-scale based on intensities of 0-255 and sets the oxygen saturation image in a second layer to display it in a color map displaying an oxygen saturation of 100% in red and an oxygen saturation of 0% in blue. In this case, one tag of the oxygen saturation DICOM file describes a weight obtained by normalizing an absorption coefficient based on a maximum value of an absorption coefficient distribution from information regarding an absorption coefficient used for the oxygen saturation calculate for each pixel of the image. The weight obtained by normalizing the absorption coefficient is used for the transmittance set for the oxygen saturation image in the second layer, and the resulting image is superimposed and is displayed in a color map from red to blue on the B mode image in the first layer.

In this case, the transmittance is reduced as the weight for the normalized absorption coefficient value decreases and is increased as the weight for the normalized absorption coefficient value increases so that a part having a large amount of blood with a higher absorption coefficient can be displayed with a higher intensity.

The tag also describes a weight for an absorption coefficient value for each voxel, and the control unit 153 may read a distribution of transmittance from the tag.

Thus, a technology can be provided which, when an operator selects oxygen saturation value and B mode image DICOM files to be displayed in a display application, can display them under conditions appropriate for interpretation and diagnosis based on information described in the tags of the DICOM files.

In this example, a weight for a transmittance is described in the tag. Instead of the scheme, an absorption coefficient DICOM file, an oxygen saturation DICOM file, and a B mode DICOM file may be read by one operation. Then, based on information representing a combination of image types of the DICOM files, the display application may calculate a weight distribution normalized for a transmittance from the absorption coefficient DICOM file. Then, an oxygen saturation image weighted by the weight distribution may be superimposed on the B mode image in the display application. The maximum value for the normalization may be a maximum luminance value in an image or may be a value input in advance or a value set by an operator through a user interface.

Example 3

According to EXAMPLE 3, DICOM images of an oxygen saturation image and total hemoglobin amount image output from a photoacoustic diagnosis apparatus are superimposed for display in a display mode corresponding to the image types. This example will be described in a case where the color maps corresponding to the image types of the DICOM files are not based on a gray-scale.

In this example, an operator first activates a display application in a PC and presses a DICOM file selection button in the display application. When the DICOM file selection button is pressed, a pop-up window being a selection screen appears, and the operator may select DICOM files to be displayed. According to this example, an operator selects an oxygen saturation image and a total hemoglobin amount image and drags and drops them onto a viewer on one screen. When the two DICOM files are dropped, the control unit 153 reads out information representing image types described in the tags. The control unit 153 obtains information regarding a color map, intensities, a transmittance, and the type name of the superimposition targets appropriate for interpretation and diagnosis corresponding to the image types. The control unit 153 then sets information for display, such as information regarding a color map, intensities, a transmittance, and the type name of the superimposition targets appropriate for interpretation and diagnosis corresponding to the image types and displays them.

In this example, the color maps corresponding to the image types read from both of the DICOM files display the oxygen saturation in red to blue and the total hemoglobin amount in yellow. Directly superimposing them may prevent clear distinction between them. In this case, the control unit 153 may read acceptable color map of the DICOM files from the tags to determine whether the superimposition results in an appropriate color map. In this example, the oxygen saturation image does not have an acceptable color map, but the total hemoglobin amount image has a gray-scale set as an acceptable color map. The total hemoglobin amount image may be displayed in the gray-scale so that superimposing the images may result in clear distinction between the superimposed images. However, when superimposing the colors of the images clarifies the superimposed part, their color maps are not necessarily to be changed.

Thus, in a case where it is difficult to distinguish between imaged superimposed using color maps corresponding to the image types of image data pieces thereof, a color map appropriate for interpretation and diagnosis may be set based on information described in the tags excluding the image types.

Second Embodiment

Configurations and processes of an image display system according to a second embodiment will be described below. Because the image display system according to this embodiment has substantially the same configuration as that of the image display system according to the first embodiment, any repetitive descriptions on the configuration will be omitted. Differences from the first embodiment will mainly be described.

The control unit 153 according to this embodiment can set a layout of a screen automatically or based on a selection made by an operator before the operator selects a DICOM file or when a plurality of DICOM files are selected on a file selection screen. The term "layout of a screen" refers to determination of the number of regions for displaying images and how they are to be arranged.

Figure 10:
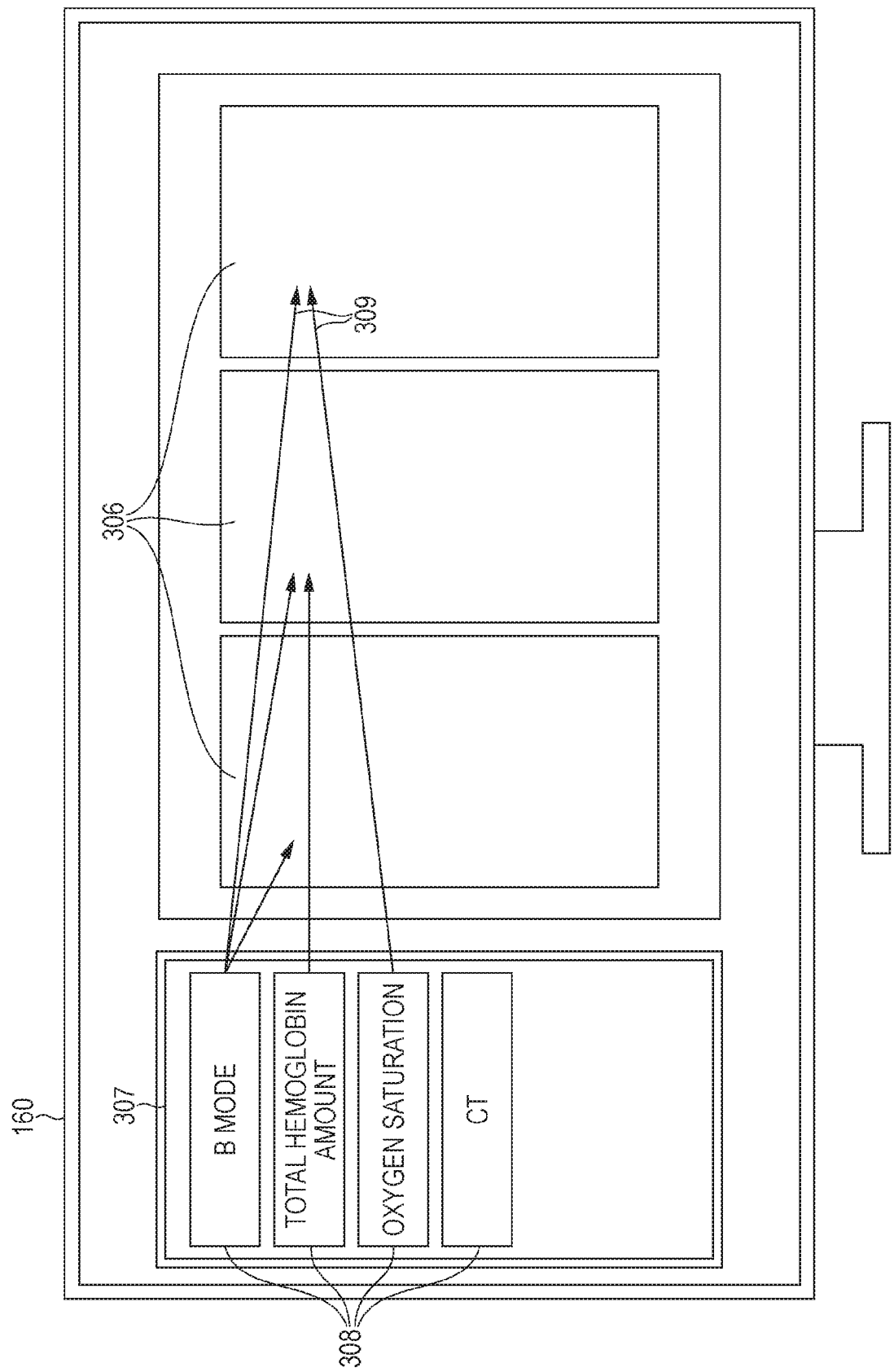
FIG. 10 illustrates a display screen on a display unit according to EXAMPLE 5.

A method which arranges images based on a layout of a screen set by an operator will be described with reference to FIGS. 9 and 10. FIG. 9 illustrates a method for selecting a layout. A layout selection screen 301 includes image display regions 302 corresponding to the numbers of screens. A layout selection button 303 may be used for layouts corresponding to four or more screens, and a button 304 may be used for selecting whether the image display regions are to be arranged vertically or horizontally with respect to the screen. Referring to FIG. 9, the image display regions are horizontally arranged. FIG. 10 illustrates an image layout method. Image display regions 306 are displayed in a viewer. A file selection window 307 of a display application displays icons 308 representing a plurality of DICOM files different from each other. The file selection window 307 displays the icons 308 such that an operator can select an arbitrary file through the icons 308. Arrows 309 represent operations for dragging and dropping an image display region on which a target DICOM file selected through the corresponding icon 308 for display by an operator. Three image display regions 306 (left, middle, and right regions) are displayed. A B mode image is dragged and dropped to the left image display region. The B mode image and a total hemoglobin amount image are dragged and dropped to the middle image display region. The B mode image and an oxygen saturation image are dragged and dropped to the right image display region. It is assumed here that a plurality of DICOM files are dropped to the middle and right image display regions and that images corresponding to the DICOM file are superimposed.

Referring to FIG. 10, DICOM files are dragged and dropped to the image display regions so that an operator can select which files are to be superimposed for display. One of the image display regions may be clicked after a layout is selected so that the file selection screen 307 appears for the image display region for selection of an image to be displayed.

As a result of drag and drop operations performed on a plurality of DICOM files to one image display region by an operator, tags of the DICOM files may not describe that they can be superimposed or may describe that the color maps corresponding to the image types of them make distinction of the images difficult. In some cases, three or more DICOM files may be dragged and dropped to one image display region. In these cases, a pop-up window may be presented to notify an operator of that the images cannot be superimposed, or a selection window may be presented for selecting another DICOM file.

According to this embodiment, an operator may select a screen layout, select images to be superimposed and drag and drop them so that the images can be appropriately superimposed in a display application based on meta-information in image data thereof.

Example 4

More specific examples will be described below. According to EXAMPLE 4, an operator may not select a layout for three or more selected DICOM files, and a display application sets a display layout for displaying them.

In this example, an operator first activates a display application in a PC, starts an image viewer, and presses a DICOM file selection button in the display application. When the operator presses the DICOM file selection button, a pop-up window being a selection screen appears so that the operator can select DICOM files to be displayed. According to this example, an operator selects, on the file selection screen, three of an oxygen saturation DICOM file, a total hemoglobin amount DICOM file, and a B mode DICOM file.

The display application may read out information representing image type of the DICOM files and read out a display mode corresponding to the combination of the image types of the selected DICOM files from a table as illustrated in FIG. 6 or FIG. 7, for example. According to this example, because the combination of the image type corresponds to No. 2, a display image 3, a display image 4, and a display image 5 are displayed on a display device.

The display mode for three or more image data pieces may be determined based on a combination of meta-information pieces other than information regarding image types.

For example, according to this example, a tag of the B mode image DICOM file may describe an oxygen saturation image and a total hemoglobin amount image as superimposition targets. On the other hand, a tag of the oxygen saturation image DICOM file may only describe a B mode image as a superimposition target, and a tag of the total hemoglobin amount image DICOM file may only describe a B mode image as a superimposition target. The control unit 153 reads out meta-information pieces on the three files to determine a superimposition target for the files. In this example, a combination of the oxygen saturation image and the B mode image and a combination of the total hemoglobin amount image and the B mode image can be used for superimposition. A two-screen image display region is set as an image layout, and details are read out from the meta-information pieces of the DICOM files. Then, based on the information pieces, the combinations are displayed on the image display region.

According to this example, when an operator select three image data pieces to be displayed, a display application can automatically determine a layout and a superimposition combination and display the superimposition image under conditions appropriate for interpretation and diagnosis.

Example 5

According to EXAMPLE 5, an operator selects a layout for image display, and the operator selects DICOM files to be displayed for image display regions in the selected layout. A display application reads the selected DICOM files and displays them based on the read detail meta-information pieces.

According to this example, an operator first activates the display application in a PC and starts an image viewer. When the operator presses a DICOM file selection button in the display application, a pop-up window being a layout selection screen appears. The operator may select a target layout from the layout selection screen. Then, a file selection screen appears, and DICOM files to be displayed may be dragged and dropped to the image display regions in the layout selected by the operator.

In this example, the operator may select a layout including three image display regions on the layout selection screen and drag and drop DICOM files of images to be displayed to the image display regions, as illustrated in FIGS. 9 and 10. Also in this example, as illustrated in FIG. 9, a B mode image is dragged and dropped to the left image display region. The B mode image and a total hemoglobin amount image are dragged and dropped to the middle image display region. The B mode image and an oxygen saturation image are dragged and dropped to the right image display region.

The control unit 153 reads out meta-information pieces in the three files and displays images under conditions appropriate for display of the DICOM images.

According to this example, in the display application, an operator may select a layout to be displayed, select images to be displayed on the image display regions, and display the images under conditions appropriate for interpretation and diagnosis.

According to this example, an operator may first select a layout and select DICOM files to be displayed, and the layout selection screen may then be displayed. These operations may be performed in any order.

Figure 11:
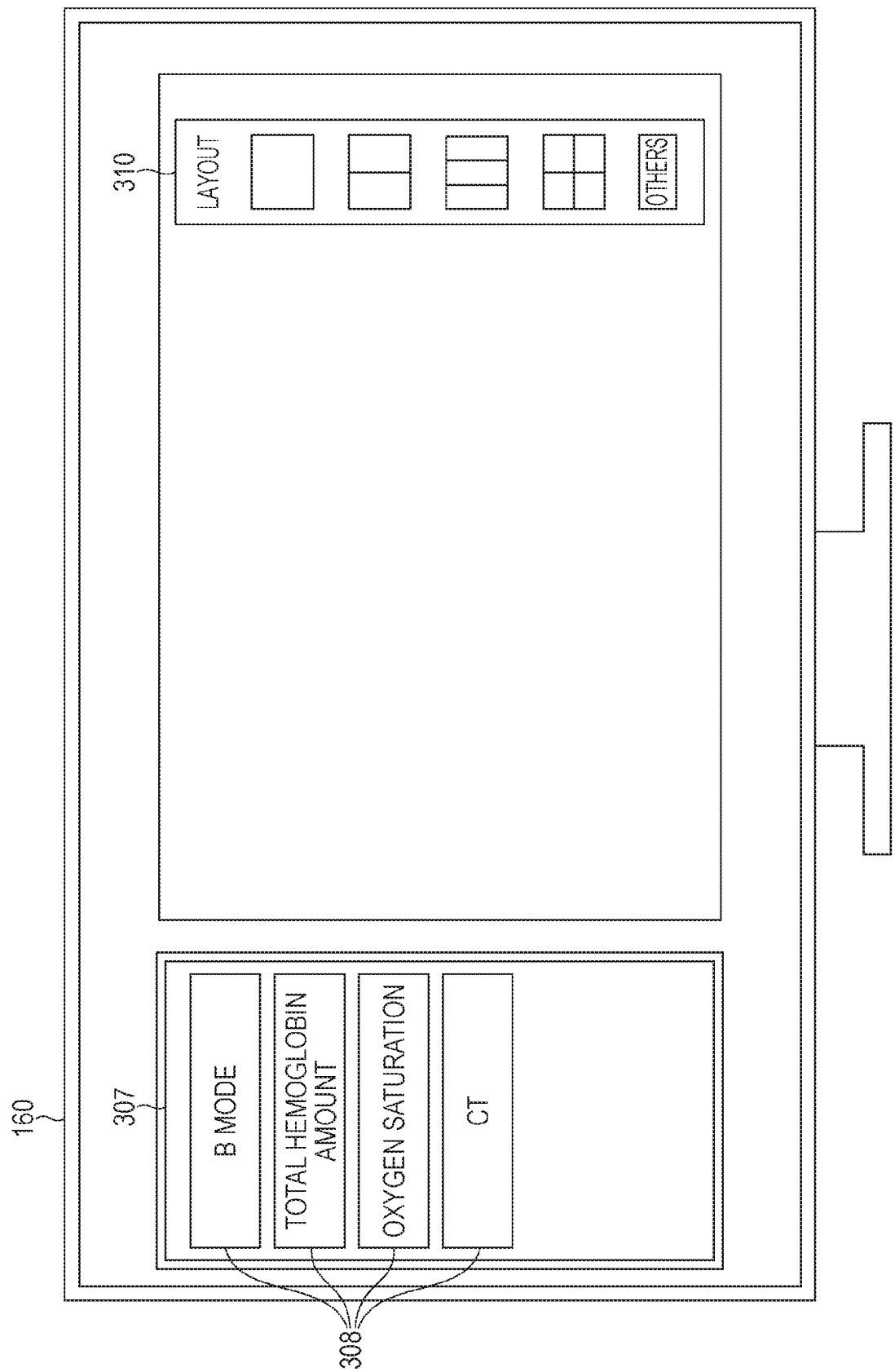
FIG. 11 illustrates a display screen on the display unit according to EXAMPLE 5.

Having described the example that an operator changes the layout to be selected every time a layout selection button is pressed for layout selection, the layout for display may be determined in any other method. For example, as illustrated in FIG. 11, a layout bar for selecting a layout may be displayed on a part of the viewer, and a layout button therein may be selected to set the selected layout. A layout bar 310 also has a button for selecting other layout than the displayed layout.

Example 6

According to EXAMPLE 6, an operator may select a layout for image display, and the operator may select DICOM files to be displayed on image display regions in the selected layout. When the images are superimposed based on color maps corresponding to the meta-information pieces on the images, it may be difficult to distinguish between the images because the color maps are similar, for example. In this case, the display application may notify it to the operator so that the operator can select another image then.

According to this example, an operator first activates a display application in a PC and starts an image viewer. When the operator presses a layout selection button in the display application, a pop-up window being a layout selection screen appears on which the operator can select a layout. Then, a file selection screen appears, and DICOM files to be displayed may be dragged and dropped to the image display regions in the layout selected by the operator.

In this example, the operator may select a layout including three image display regions on the layout selection screen and drag and drop DICOM files of images to be displayed to the image display regions, as illustrated in FIGS. 9 and 10. In this embodiment, a B mode image is dragged and dropped to the left image display region. The B mode image and a total hemoglobin amount image are dragged and dropped to the middle image display region. The total hemoglobin amount image and an oxygen saturation image are dragged and dropped to the right image display region.

The control unit 153 reads out meta-information pieces in the three files and sets a display mode under conditions appropriate for display of the DICOM images. When two files are dragged and dropped to the right image display region, the color maps of the images are set based on the meta-information pieces of the files. If it is determined that superimposition of the color maps corresponding to the meta-information pieces of the image files prevents distinction of the images, a pop-up window appears as illustrated in FIG. 12 to notify it to the operator. When an acceptable color map enabling distinction of the images is available, the images may be superimposed based on the acceptable color map by notifying it (for example, the total hemoglobin amount is displayed in gray-scale), as will be described below.

In this example, the color map corresponding to the meta-information of the oxygen saturation image is blue to red, and the tag does not describe an acceptable color map. On the other hand, the color map corresponding to the meta-information of the total hemoglobin amount image is yellow, and the tag describes gray-scale as an acceptable color map. In this case, the color map of the total hemoglobin amount image may be changed to gray-scale so that the superimposition image can be displayed in which both of the images can be distinguished. Accordingly, the display application sets the color map of the total hemoglobin amount image to gray-scale, and the two images are superimposed.

With a notification on a pop-up window that a combination of the selected images is not appropriate for superimposition, whether they are to be superimposed or not may be displayed on the pop-up window or a GUI for setting a display mode such as a color map may be displayed thereon.

Example 7

According to EXAMPLE 7, a plurality of DICOM files captured at different times and having different image types are selected, a display application determines a correspondence in time between images so that images corresponding to captured times that are neighboring in time are superimposed for display.

According to this example, an operator first activates a display application in a PC and starts an image viewer. When the operator presses a layout selection button in the display application, a pop-up window being a layout selection screen appears on which the operator can select a layout with one image display region. Then, a file selection screen appears, and an operator may select a DICOM file to be displayed.

FIG. 13 illustrates a file selection screen and an image display region on the viewer. FIG. 13 illustrates a file selection screen 401. The screen 401 includes DICOM files of three B mode images captured at different times, three oxygen saturation images captured at different times by a photoacoustic diagnosis apparatus, and one CT image. Here, a B mode image and an oxygen saturation image in selection are emphasized by thick lines. The number given to each of the DICOM files represents captured time (year, month, day, hour, minute, second) as a meta-information piece associated with the file. The control unit 153 can determine superimposition targets based on the meta-information pieces representing captured times. FIG. 13 further illustrates an image display region sign 402 on the viewer. FIG. 13 further illustrates a tumor 403A in the B mode image and a blood vessel 403B in the oxygen saturation image. Explanatory notes 404 are associated with the images. FIG. 14 illustrates details of the explanatory notes 404.

In order to superimpose images here, the captured times of the target DICOM files to be superimposed are not necessarily completely matched. Images captured at times that are neighboring in time may be superimposed. The control unit 153 may determine the image types to be superimposed based on meta-information pieces of the DICOM files thereof. FIG. 13 illustrates a superimposition image of a B mode image having the lowest number representing its captured time and an oxygen saturation image having the highest number representing captured time. The B mode image having the lowest number representing its captured time here represents the B mode image arranged at the top on the file selection screen 401. The oxygen saturation image having the highest number representing captured time represents the fourth oxygen saturation image from the top on the file selection screen 401. In the example illustrated in FIG. 13, a superimposition image corresponding to one captured time is displayed in one image display region and is changed to another superimposition image corresponding to a different captured time in response to a click with a mouse or an operation on a wheel. Having described that images to be superimposed are determined based on their captured times, they may be determined based on coordinate positions such as coordinate positions with respect to an apparatus or coordinate positions with respect to an internal organ, for example.

FIG. 15 illustrates a mode for displaying in parallel superimposition images of images captured at neighboring times. FIG. 15 illustrates explanatory notes 404 and superimposition images 405 corresponding to a plurality of captured time different from each other (or superimposition images captured at times neighboring to each other). The explanatory notes may be presented as a pop-up window to be displayed in response to a right click after a target image is selected and is activated or a selection of an information display button on the application. Illustrating in FIG. 15 that three superimposition images displayed, superimposition images the number of which is equal to the number of possible combinations may be displayed, or the number and size of superimposition images to be displayed may be defined such that an operator can visually recognize the images on the viewer. Alternatively, a click or a wheel operation may be performed on one of three images displayed on the viewer to feed superimposition images arranged in order of captured times from right to left by keeping the three image display ranges. Thus, superimposition images more than the number of display regions can be displayed. An operator may select a layout from a selection screen. When an operator selects a plurality of files, one of such a captured-time-based feeding mode and a parallel display mode may be selected. A plurality of superimposition images may be displayed in an overlapping manner, as illustrated in FIG. 16. FIG. 16 illustrates overlapped superimposition images 406 displayed in time series. An operator may click or operate a mouse wheel to change the image displayed on the forefront of the time-series superimposition images 406. The plurality of superimposition images may be displayed such that the order of captured times can be identified.

Having described that, according to this example, a plurality of single frame DICOM files is selected and is superimposed on corresponding DICOM files for display, multiframe DICOM files of different image types may be selected, and corresponding images thereamong may be superimposed for display. The number of frames of the selected multiframe DICOM files of different image types may not correspond to each other. The frames may be superimposed from the first frame for display, or frames having correspondence information on their tags may only be displayed in accordance with a feeding operation performed by an operator.

Example 8

According to EXAMPLE 8, a plurality of DICOM files captured at different times and of different image types are superimposed to display the images in synchronism with other data from, for example, an electrocardiograph.

In this example, an operator first activates a display application in a PC and starts an image viewer. An operator may activate a file selection screen and selects DICOM files to be superimposed (in this case, a DICOM file of an oxygen saturation image and a DICOM file of a B mode image). Next, the operator may select other data such as electrocardiogram data to be synchronized. Then, based on the captured times of the files, a superimposition image and the electrocardiogram data are displayed in synchronization. The display application according to this example, a display mode may be determined based on a combination of image types of DICOM files and data (electrocardiogram data) to synchronize with the files.

Figure 17:
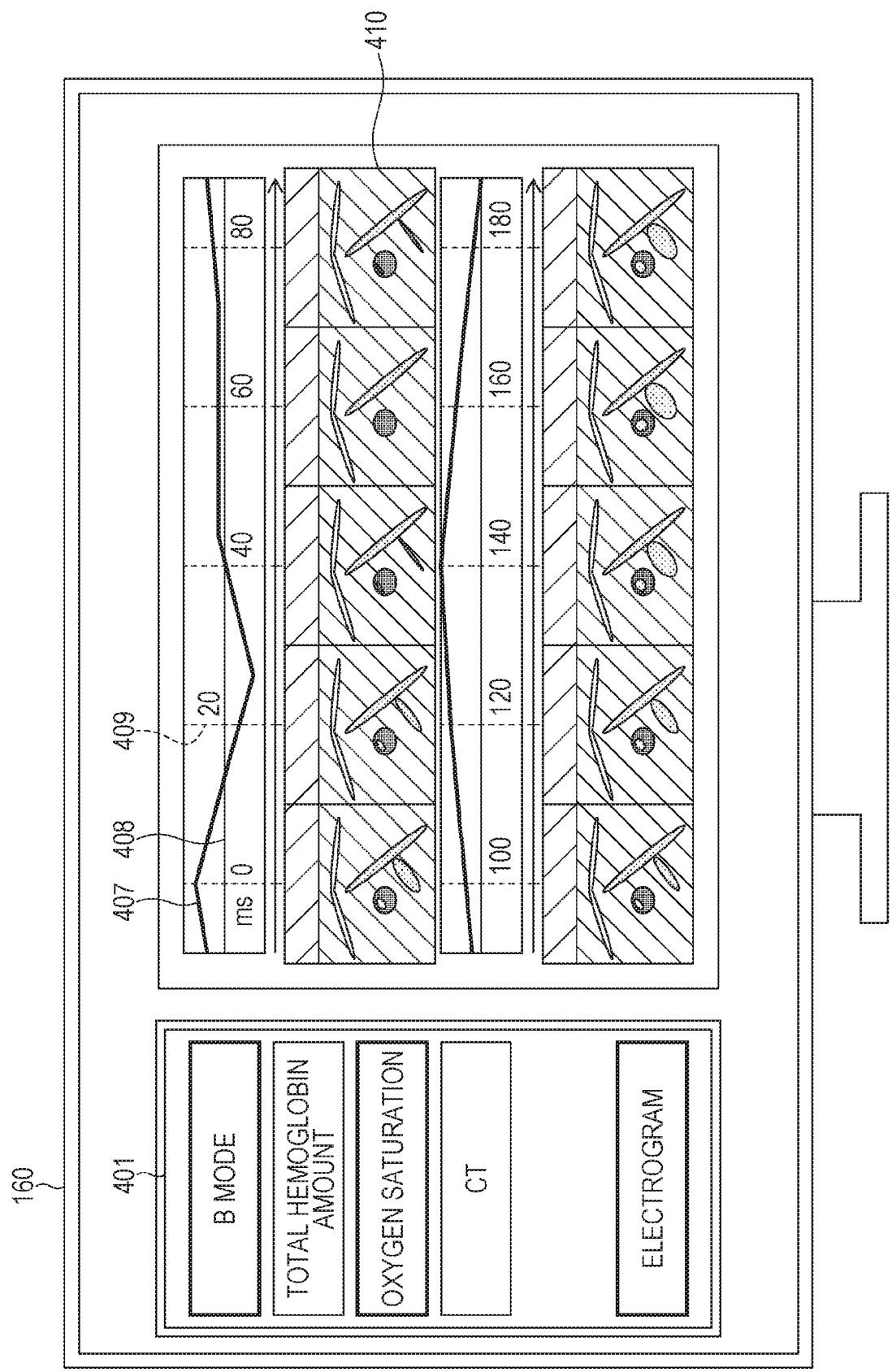
FIG. 17 illustrates a display screen on the display unit according to EXAMPLE 7.

FIG. 17 illustrates a viewer of a display application according to this example. FIG. 17 illustrates heartbeat data 407 from an electrocardiograph, a clock time (ms) 408, which is indicated by a numerical value, from 0 defined at a certain peak in an electrocardiogram data, captured times 409, which are indicated by broken lines, of superimposition images, and superimposition images 410 of a B mode image and an oxygen saturation image. Each of the captured times 409 is determined based on the captured time of one of a plurality of images to be superimposed or an intermediate clock time of the captured times.

Referring to FIG. 17, an oxygen saturation image and a B mode image are superimposed, and superimposition images thereof are displayed in parallel in order of the captured times. Referring to FIG. 17, electrocardiogram data are saved in association with captured times, and each of the captured times 409 indicated by broken lines represents a correspondence between a captured time of heartbeat data of the electrocardiogram data and a captured time of a superimposition image. In FIG. 17, the upper right end image and the lower left end image are an identical superimposition image. Thus, even in limited display regions, an operator can easily visually recognize time relations between images.

The display period (time length) of an electrocardiograph may be changed so that the superimposition image to be displayed can be updated based on the display period of the electrocardiograph. All of superimposition images may not be displayed in parallel with some display periods of an electrocardiograph. In this case, the number of superimposition images to be displayed may be changed so that the number of images corresponding to the display period of the electrocardiograph may be displayed.

Third Embodiment

Configurations and processes of an image display system according to a third embodiment will be described below. In the image display system according to this embodiment, DICOM files from a plurality of modalities saved in a server functioning as a storage unit can be viewed and be searched from various PCs. Differences from the first embodiment will mainly be described below.

Figure 18:
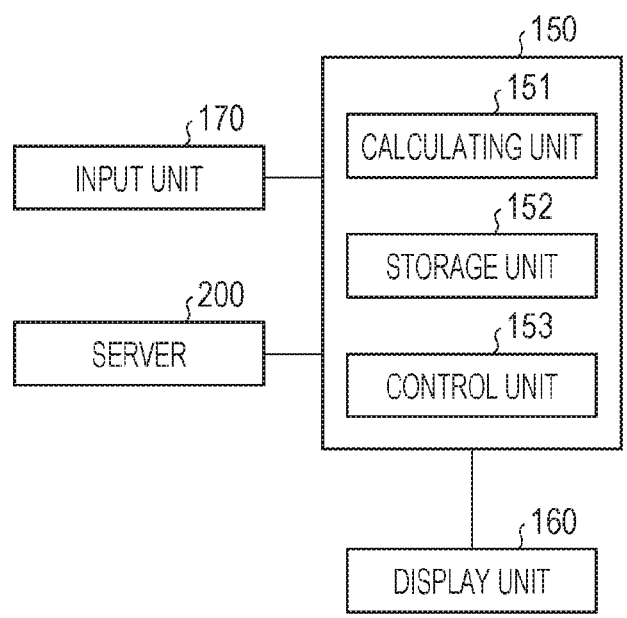
FIG. 18 is a schematic diagram illustrating a configuration of an image display system according to a third embodiment.

FIG. 18 is a schematic diagram illustrating a configuration of an image display system according to this embodiment. The image display system according to this embodiment does not have the probe 180 and the signal collecting unit 140 corresponding to modality functionality, unlike the first embodiment. On the other hand, the image display system according to this embodiment includes a server 200 configured to store image data acquired by a modality. A system having a function of display control to be performed by the computer 150 may be called an image display system.

The server 200 receives data from a modality having a function of transmitting a DICOM file and stores the data. In response to a request from the control unit 153, the server 200 can search the corresponding DICOM file and can transmit information. Information saved from the server 200 to a server in a data center over a network can be accessed from a terminal connected to the network.

The control unit 153 is communicable with the server 200 and ca search a DICOM file stored in the server 200. When an operator selects one DICOM file, the control unit 153 can read meta-information on the DICOM file and obtain a patient ID so that the patient ID can be searched on the server 200. In this case, the control unit 153 can obtain a DICOM file with the identical patient ID or meta-information on an associated DICOM file. The control unit 153 may read out meta-information pieces on a plurality of DICOM files of one patient and may display a superimposition image on the display unit 160 in a superimposition style based on a combination of the meta-information pieces.

Alternatively, an operator may not designate one DICOM file but may designate an information piece such as a patient ID, a captured date, an image type, and a captured hospital through a search window in the display application so that the corresponding image data can be searched on the server 200. In other words, an operator may use the input unit 170 to input a meta-information piece such as a patient ID, and the control unit 153 searches on the server 200 based on the input meta-information to obtain an associated DICOM file. A DICOM file associated with one patient may be obtained if information representing that the patient is identical to that with the patient ID is written in a tag of the DICOM file even when the DICOM file has a different patient ID because, for example, it is captured at a different hospital.

Having described that, according to this embodiment, one computer 150 views and searches image data on the server 200, a plurality of computers may view and search image data on the server 200.

Example 9

More specific examples will be described below. According to EXAMPLE 9, an operator may select a DICOM file saved in advance in the storage unit 152 so that the control unit 153 can read a patient ID of the DICOM file, search a related DICOM file on the server 200, and transmit it to the control unit 153. The control unit 153 can display the DICOM file transmitted from the server 200 together with a file name and a superimposition image as a file related to the selected DICOM file.

Figure 19:
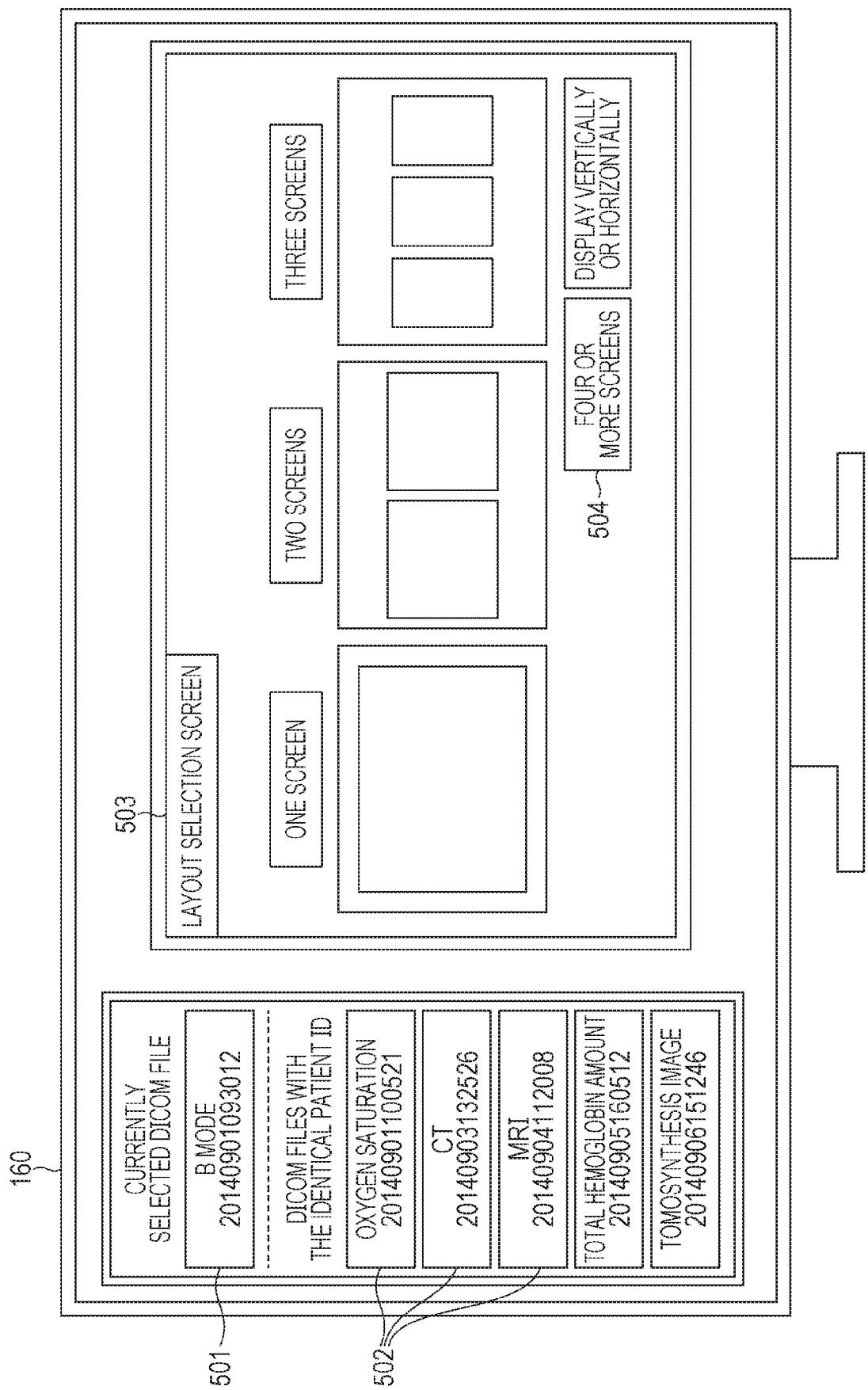
FIG. 19 illustrates a display screen on a display unit according to EXAMPLE 9.

FIG. 19 illustrates a screen on which an operator may double-click to select one DICOM file stored in advance in the storage unit 152 and display it on the display unit 160 in response to a press of an image layout button. A DICOM file 501 may be selected by double-clicking. When the DICOM file 501 is selected, the control unit 153 reads a patient ID of the DICOM file and searches the patient ID on the server 200. A DICOM file 502 with the same patient ID is found by the search. A layout selection screen 503 is displayed on the viewer. In this example, in order to display four screens, an operator may press a button 504 for displaying four or more screens and select a layout of image display regions for four screens.

Figure 20:
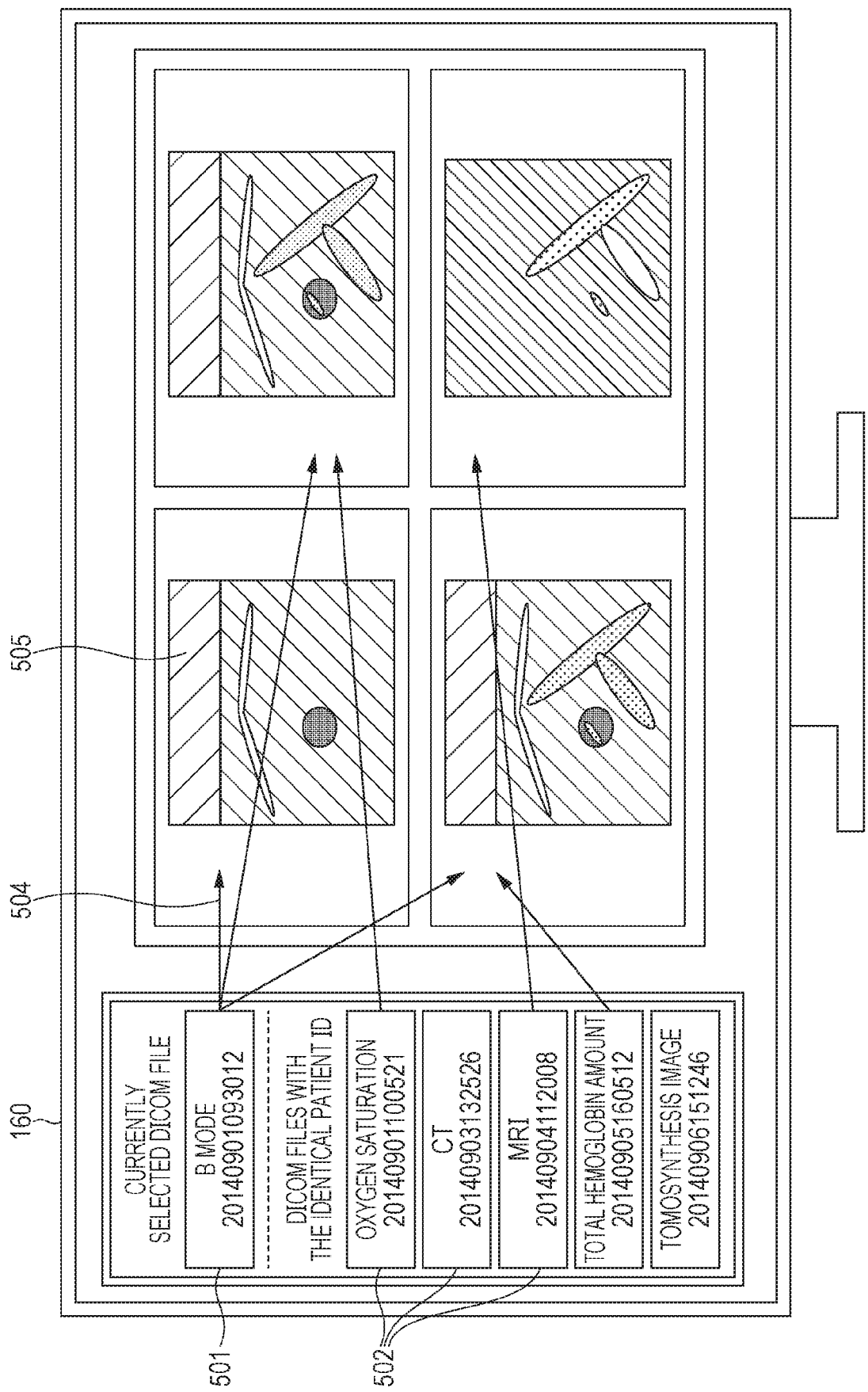
FIG. 20 illustrates a display screen on the display unit according to EXAMPLE 9.

FIG. 20 illustrates a result of a selection operation on a four-screen layout and a subsequent drag and drop operation on images to be displayed to the image display regions. The drag and drop operation on the selected DICOM files is referred by reference 504. In this example, four image display regions 505 are provided in the viewer. Images are displayed on the image display regions. A B mode image is only displayed on the upper left screen, a superimposition image of the B mode image and a total hemoglobin amount image is displayed on the lower left screen. A superimposition image of the B mode image and an oxygen saturation image is displayed on the upper right screen, and an MRI image is only displayed on the lower right screen. Thus, the display position of tissue not present in the B mode image displayed alone can be identified when the B mode image is superimposed on an oxygen saturation image or a total hemoglobin amount image that is functional information. Those images can also be compared with an image output from another modality such as an MRI.

In this example, an operator first activates a display application in a PC and starts an image viewer. When the operator presses a file selection button, the control unit 153 selects and reads a DICOM file stored in advance in the storage unit 152.

The control unit 153 reads meta-information of the selected DICOM file to obtain a patient ID. The obtained patient ID is searched on the server 200, and the server 200 transmits the DICOM file obtained by the searching to the control unit 153.

The control unit 153 displays the transmitted DICOM on the file selection screen on the display unit 160. The operator may select a DICOM to be displayed other than the already displayed image from the displayed file selection screen and superimpose the selected image on the already displayed image. In this case, image display settings may be set based on the meta-information read by the control unit 153, like the aforementioned embodiments. Display forms other than superimposition are also applicable. For example, the selected image may be displayed together with the already displayed image side by side.

Example 10

According to EXAMPLE 10, one of a plurality of multiframe DICOM images of different types is positioned by changing its size and orientation on a viewer, and the other images are superimposed thereon for synchronization display.

Figure 21:
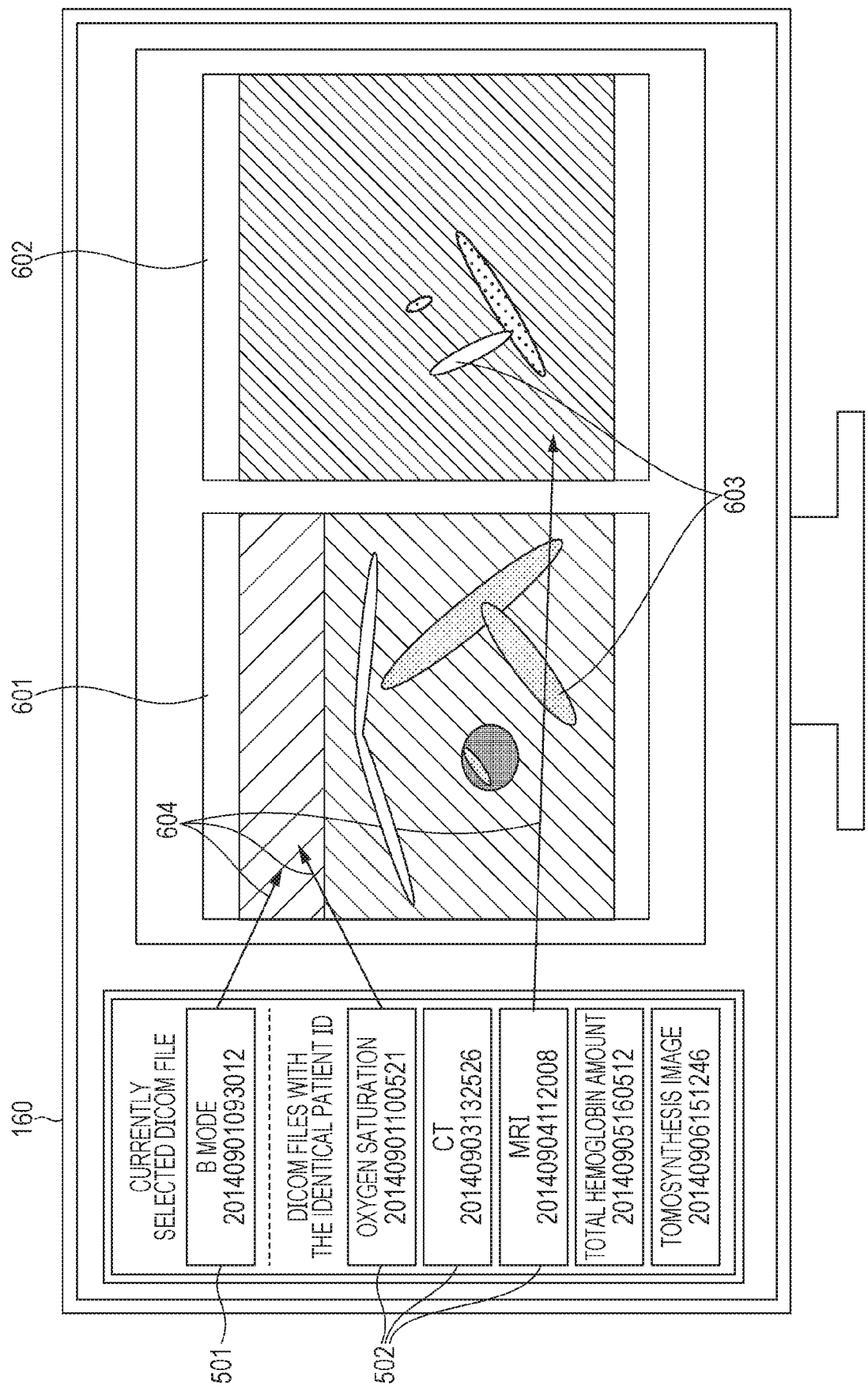
FIG. 21 illustrates a display screen on the display unit according to EXAMPLE 9.

FIG. 21 illustrates a viewer according to this example. One image display region 601 in the viewer displays one section where B mode images and oxygen saturation images the number of slices of which is equal to the number of frames are superimposed. Another image display region 602 in the viewer displays a section of a multiframe MRI image the number of slices and the size of which are different from those of an oxygen saturation image. An identical living body tissue 603 in the images has different sizes and orientations between the images. Arrows 604 indicate drag and drop operations.

Figure 22:
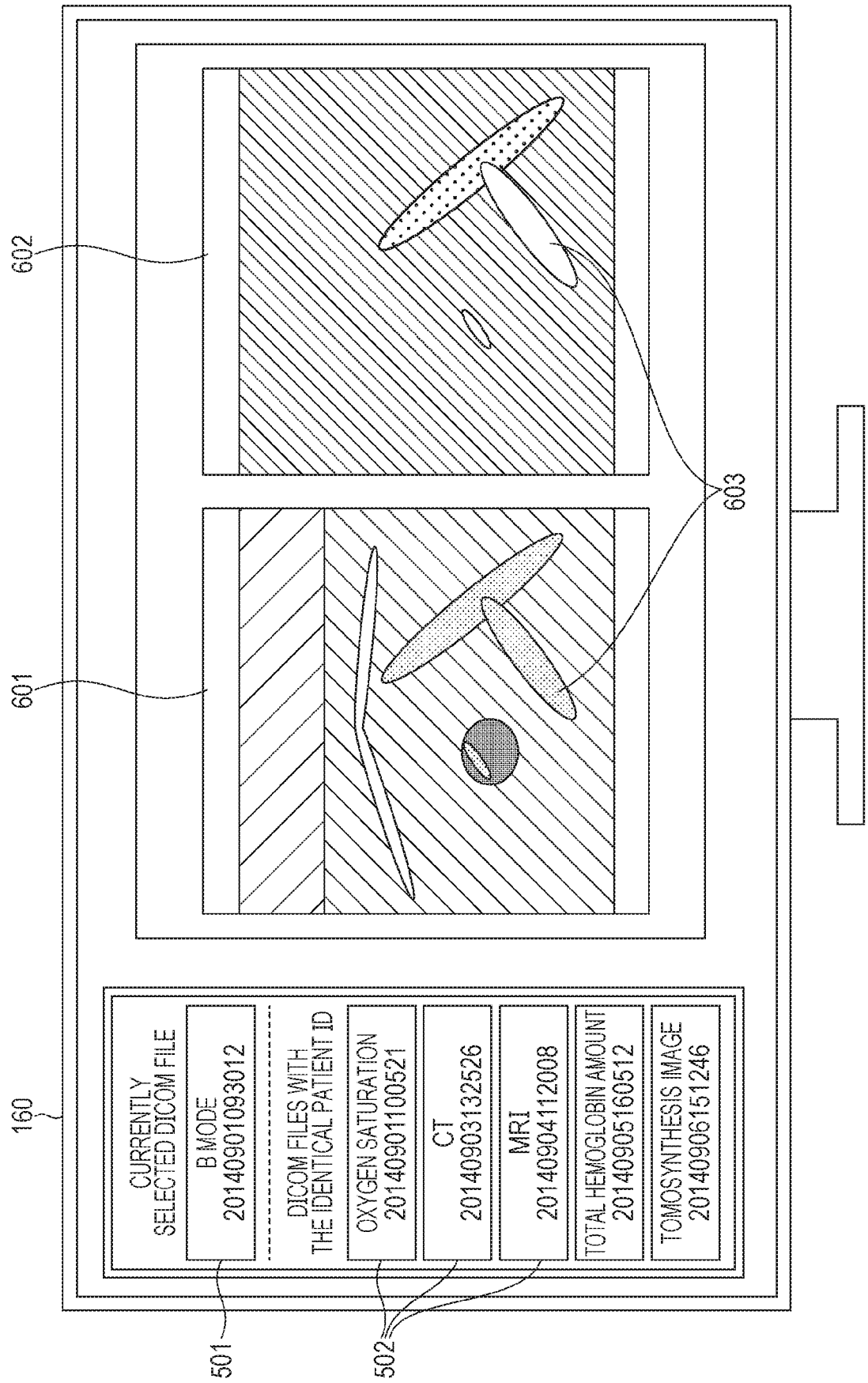
FIG. 22 illustrates a display screen on the display unit according to EXAMPLE 9.

Here, the positioning is performed by clicking and dragging (or clocking and pulling an image) on the right image display region in the image viewer to change the orientation of the image and enlarge the size of the image. FIG. 22 illustrates a result of the positioning where the size and the orientation of the living body tissue can be positioned. Then, a total hemoglobin amount image DICOM file is dragged and dropped to the right image display region in the viewer to superimpose the total hemoglobin amount image DICOM file on the living body tissue image having the positioned shape and orientation. In a case where slices are fed under the state, if the slice intervals in the images in displayed in the image display regions are different, a nearest neighbor slice of the slice coordinates of one of the displayed DICOM images may be displayed.

In this example, one section of a multiframe image is used to change the size and orientation. However, a three-dimensional image may be displayed in a viewer, and the size and orientation thereof may be changed. In this case, the three-dimensional image may be generated by volume rendering, for example, from a multiframe image being a set of two-dimensional slices and may be changed in size and orientation and may be displayed or superimposed with the number of slices and pixel pitches corresponding to the superimposition target image.

Thus, DICOM images output from various modalities and of various types and conditions may be positioned by changing their orientations and sizes by an operator so that they can be displayed freely under condition appropriate for interpretation and diagnosis.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-198891, filed Oct. 7, 2016, which is hereby incorporated by reference herein in its entirety.

The invention claimed is:

1. An image display system comprising:
at least one memory storing a program; and
at least one processor that when executing the program, causes the image display system to:
obtain a first image data piece;
obtain a first meta-information piece including information representing an image type of the first image data piece;
obtain a second image data piece;
obtain a second meta-information piece including information representing an image type of the second image data piece; and
determine a superimposition style corresponding to a combination of the first and second meta-information pieces based on the first and second meta-information pieces; and
display a superimposition image of the first and second image data pieces in the superimposition style on a display unit,
wherein the determine the superimposition style includes determining a superimposing order of the first and second image data pieces based on the combination of the first and second meta-information pieces and the display the superimposition image includes displaying the superimposition image by superimposing the first and second image data pieces in the superimposing order.

2. The image display system according to claim 1, wherein the determine the superimposition style corresponding to a combination of image types of the first and second image data pieces.

3. The image display system according to claim 1, wherein the determine the superimposition style includes determining color schemes of the first and second image data pieces as the superimposition style based on the first and second meta-information pieces and the display the superimposition image includes displaying the superimposition image of the first and second image data piece in the color schemes on the display unit.

4. The image display system according to claim 1, wherein the at least one processor causes the image display system to
determine a display layout of an image of at least one image data piece of the first and second image data pieces and the superimposition image based on the first and second meta-information pieces; and
display the image of the at least one image data piece of the first and second image data pieces and the superimposition image side by side in the display layout on the display unit.

5. The image display system according to claim 1, wherein the at least one processor further causes the image display system to:
obtain information representing a relationship between a combination of meta-information pieces and a superimposition style,
wherein the determine the superimposition style corresponding to a combination of the first and second meta-information pieces with reference to the information representing the relationship.

6. The image display system according to claim 1, wherein the at least one processor causes the image display system to determine whether the first and second image data pieces are appropriate to be superimposed or not based on the first and second meta-information pieces and displaying the determination result on the display unit.

7. The image display system according to claim 1, wherein the obtain the first image data piece includes reading out the first and second image data pieces saved in a picture archiving and communication system to obtain the first and second image data pieces.

8. The image display system according to claim 1, wherein the obtain the first image data piece includes obtaining first and second image data pieces determined based on a user's instruction.

9. The image display system according to claim 1, wherein the first and second meta-information pieces are information regarding image types store in data files generated based on a DICOM format.

10. The image display system according to claim 1, wherein a display mode further includes at least one selected from the group of a color scheme of the superimposition image, a transmittance of the image, and a luminance range.

11. The image display system according to claim 1, wherein the first and second image data pieces are medical image data pieces obtained from modalities different from each other.

12. The image display system according to claim 1, wherein the at least one processor causes the image display system to display icons representing the plurality of image data pieces on the display unit,
wherein the icons are displayed such that a combination of image data pieces appropriate to be superimposed from the plurality of image data pieces based on the first and second meta-information pieces can be identified.

13. The image display system according to claim 12, wherein the at least one processor causes the image display system to display a combination of image data pieces appropriate to be superimposed from the plurality of image data pieces based on information representing image type regarding the plurality of image data pieces as the first and second meta-information pieces such that the combination can be identified.

14. An image display method comprising:
obtaining a first image data piece;
obtaining a first meta-information piece including information representing an image type of the first image data piece;
obtaining a second image data piece;
obtaining a second meta-information piece including information representing an image type of the second image data piece;
determining a superimposition style corresponding to a combination of the first and second meta-information pieces based on the first and second meta-information pieces; and
displaying a superimposition image of the first and second image data pieces in the superimposition style on a display unit,
wherein the determining the superimposition style includes determining a superimposing order of the first and second image data pieces based on the combination of the first and second meta-information pieces, and the displaying the superimposition image includes superimposing the first and second image data pieces in the superimposing order.

15. A non-transitory computer-readable storage medium which stores a program causing a computer to execute the image display method according to claim 14.

16. An image display method comprising:
selecting a plurality of image data files to be displayed as superimposed images from image data files stored in an image storage server;
obtaining a plurality of image data corresponding to the selected plurality of files;
obtaining information indicating a combination of meta-information associated with the plurality of image data;
determining a superimposing order and a transmittance of the plurality of image data on the basis of information indicating the combination of the meta-information associated with the plurality of image data corresponding to the plurality of image data files; and
displaying a superimposition image of the plurality of image data, on a display unit, on the basis of the superimposing order and the transmittance.

17. A non-transitory computer-readable storage medium which stores a program causing a computer to execute the image display method according to claim 16.

18. An image display system comprising:
at least one memory storing a program; and
at least one processor that when executing the program, causes the image display system to:
select a plurality of image data files to be displayed as superimposed images from image data files stored in an image storage server;
obtain a plurality of image data corresponding to the selected plurality of files;
obtain information indicating a combination of meta-information associated with the plurality of image data;

determine a superimposing order and a transmittance of the plurality of image data on the basis of information indicating the combination of the meta-information associated with the plurality of image data corresponding to the plurality of image data files; and display a superimposition image of the plurality of image data, on a display unit, on the basis of the superimposing order and the transmittance.

* * * * *